United States Patent
Wanders

(10) Patent No.: US 10,422,738 B2
(45) Date of Patent: *Sep. 24, 2019

(54) SYSTEMS AND METHODS FOR IMAGING FLUID SAMPLES

(71) Applicant: Iris International, Inc., Chatsworth, CA (US)

(72) Inventor: Bart J Wanders, Trabuco Canyon, CA (US)

(73) Assignee: Iris International, Inc., Chatsworth, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 15/519,407

(22) PCT Filed: Oct. 17, 2014

(86) PCT No.: PCT/US2014/061221
§ 371 (c)(1),
(2) Date: Apr. 14, 2017

(87) PCT Pub. No.: WO2016/060691
PCT Pub. Date: Apr. 21, 2016

(65) Prior Publication Data
US 2017/0268984 A1      Sep. 21, 2017

(51) Int. Cl.
*G01N 15/14* (2006.01)
*G01N 21/05* (2006.01)
(Continued)

(52) U.S. Cl.
CPC ....... *G01N 15/1463* (2013.01); *A61B 5/0059* (2013.01); *G01N 15/1404* (2013.01);
(Continued)

(58) Field of Classification Search
CPC .... G01N 15/1463; G01N 21/85; G01N 21/05; G01N 15/1404; G01N 15/1459;
(Continued)

(56) References Cited

U.S. PATENT DOCUMENTS

| 4,428,669 A | 1/1984 | Bessis |
| 5,007,732 A | 4/1991 | Ohki |

(Continued)

FOREIGN PATENT DOCUMENTS

| JP | 63134958 | 7/1988 |
| JP | 05296915 A | 11/1993 |

(Continued)

OTHER PUBLICATIONS

Halder et al, Digital camera based spectrometry for the development of point of care anemia detection on ultra low volume whole blood sample (Year: 2017).*

(Continued)

*Primary Examiner* — Shan E Elahi
(74) *Attorney, Agent, or Firm* — Schwegman Lundberg & Woessner, P.A.

(57) ABSTRACT

Systems and methods for imaging a plurality of blood fluid samples or other types of samples include processing at least a portion of a sample to enhance imageability of certain particles in that portion and subsequently imaging the sample portion. In some instances, processing and imaging of various samples may be staged in a manner to optimize throughput of the system or method.

20 Claims, 23 Drawing Sheets

(51) Int. Cl.
*G01N 21/85* (2006.01)
*A61B 5/00* (2006.01)
*G01N 15/00* (2006.01)

(52) U.S. Cl.
CPC ..... *G01N 15/1425* (2013.01); *G01N 15/1459* (2013.01); *G01N 21/05* (2013.01); *G01N 21/85* (2013.01); *G01N 2015/0065* (2013.01); *G01N 2015/144* (2013.01); *G01N 2015/1409* (2013.01)

(58) Field of Classification Search
CPC ....... G01N 15/1425; G01N 2015/1409; G01N 2015/144; G01N 2015/0065; A61B 5/0059
USPC .......................................................... 348/77
See application file for complete search history.

(56) References Cited

U.S. PATENT DOCUMENTS

| | | | |
|---|---|---|---|
| 5,159,403 A | 10/1992 | Kosaka | |
| 5,412,466 A | 5/1995 | Ogino | |
| 5,690,895 A | 11/1997 | Matsumoto | |
| 6,365,106 B1* | 4/2002 | Nagai ................. | G01N 15/1404 356/246 |
| 7,351,221 B2 | 4/2008 | Trombley, III et al. | |
| 7,799,575 B2 | 9/2010 | Jiang | |
| 9,316,635 B2 | 4/2016 | Farrell | |
| 9,322,752 B2 | 4/2016 | Wanders | |
| 9,429,524 B2* | 8/2016 | Wanders ............ | G01N 15/1404 |
| 9,459,196 B2* | 10/2016 | Zahniser ................. | G01N 15/14 |
| 2005/0180885 A1 | 8/2005 | Tateishi | |
| 2006/0050946 A1 | 3/2006 | Mitchison | |
| 2007/0020721 A1* | 1/2007 | Yoshida ............. | G01N 15/1459 435/34 |
| 2008/0038738 A1 | 2/2008 | Welgum | |
| 2011/0151502 A1* | 6/2011 | Kendall ............... | G01N 1/2813 435/39 |
| 2013/0024130 A1* | 1/2013 | Zahniser ................ | G16H 40/63 702/21 |
| 2013/0201317 A1* | 8/2013 | Ortyn ................... | G01N 15/147 348/77 |
| 2014/0273067 A1* | 9/2014 | Wanders ............ | G01N 33/5094 435/29 |
| 2014/0273068 A1 | 9/2014 | Wanders | |
| 2014/0296089 A1* | 10/2014 | Holmes ................ | G01N 35/026 506/9 |
| 2014/0315238 A1 | 10/2014 | Farrell | |
| 2014/0329265 A1 | 11/2014 | Wanders | |
| 2014/0356938 A1* | 12/2014 | Kendall ............... | G01N 1/2813 435/288.7 |
| 2016/0041083 A1* | 2/2016 | Wanders ............ | G01N 33/5094 435/39 |
| 2016/0109372 A1* | 4/2016 | Wanders ........... | G01N 15/1404 356/40 |
| 2016/0258858 A1* | 9/2016 | Kendall ............... | G01N 1/2813 |
| 2017/0091528 A1* | 3/2017 | Savvides ............. | G06K 9/0014 |
| 2017/0370820 A1* | 12/2017 | Wanders ............ | G01N 33/5094 |
| 2018/0149576 A1* | 5/2018 | Wanders ............ | G01N 33/5094 |

FOREIGN PATENT DOCUMENTS

| | | |
|---|---|---|
| JP | 09281027 A | 10/1997 |
| JP | 2000214070 A | 8/2000 |
| WO | 2016/060691 | 4/2016 |

OTHER PUBLICATIONS

International Search Report and Written Opinion of PCT/US2014/061221 dated Jun. 23, 2015, 12 pages.
JP2017-520398 received an Office Action dated Oct. 30, 2018, 10 pages.

\* cited by examiner

SYSTEMS AND METHODS FOR IMAGING FLUID SAMPLES

RELATED FIELDS

Systems and methods for analysis of particles, including imaging of particles in fluid samples, using wholly or partly automated devices to discriminate and quantify particles such as blood cells in the sample. For example, the systems and methods of the present disclosure may be useful for counting and/or characterizing particles in biological fluids such as red blood cells, reticulocytes, nucleated red blood cells, platelets, and for image and morphologically-based white blood cell differential counting, categorization, sub-categorization, characterization and/or analysis.

BACKGROUND

Blood cell analysis is one of the more commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, the five major types or subclasses of white blood cells (WBCs)—neutrophils, lymphocytes, monocytes, eosinophils, and basophils—each have different shapes and functions. Red blood cell (RBCs) subclasses may include reticulocytes and nucleated red blood cells. The number and appearances of the blood cells or other particles in a sample may differ according to pathological conditions, cell maturity and other causes.

Complete Blood Counts (CBC) and other blood cell counts estimating the concentration of and otherwise characterizing RBCs, WBCs or platelets can be done manually or using an automated analyzer. When blood cell counts are done manually, a drop of blood is applied to a microscope slide as a thin smear, which may be manually examined under a light microscope. Histological dyes and stains may be used to stain cells or cellular structures. For example, Wright's stain is a histologic stain that has been used to stain blood smears for examination under a light microscope.

An automated CBC can employ instruments or methods to differentiate between different types of cells that include RBCs, WBCs and platelets, which can be counted separately. For example, a counting technique requiring a minimum particle size or volume might be used to count only large cells.

Some automated analyzers, including some automated analyzers using flow cytometry, count the number of different particles or cells in a blood sample based on impedance or dynamic light scattering as the individual particles or cells pass through a sensing area along narrow flow path such as a small tube. Flow cytometry methods have been used to detect particles suspended in a fluid, such as cells in a blood sample, and to analyze the particles as to particle type, dimension, and volume distribution so as to infer the concentration of the respective particle type or particle volume in the blood sample.

Automated systems using dynamic light scattering or impedance have been used to obtain a Complete Blood Count, which, in some instances, may include one or more of: total white blood cell count, total cellular volume of red blood cells (RBC distribution), hemoglobin HGB (the amount of hemoglobin in the blood), mean cell volume (MCV) (mean volume of the red cells), MPV (mean PLT volume), hematocrit (HCT), MCH (HGB/RBC) (the average amount of hemoglobin per red blood cell), and MCHC (HGB/HCT) (the average concentration of hemoglobin in the cells). Automated or partially automated processes have been used to facilitate white blood cell five part differential counting and other blood sample analyses.

Some automated analyzers use image based techniques to count or otherwise analyze particles in a fluid flowing through a flow cell. Some example of systems using imaging techniques and flow cells are described in U.S. Pat. No. 6,825,926 to Turner et al., U.S. Pat. No. 6,184,978 to Kasdan et al., U.S. Pat. No. 6,424,415 to Kasdan et al., and U.S. Pat. No. 6,590,646 to Kasdan et al.

While currently known techniques, systems and methods for particle counting (such as cells in a blood fluid or other types of particles in a fluid) and other diagnostic analysis can provide real benefits to doctors, clinicians, and patients, further improvements is still possible.

BRIEF SUMMARY

In some embodiments, a method for imaging a plurality of blood fluid includes: receiving a first blood fluid portion in a sample analysis system; processing the first portion so as to enhance imageability of a first type of cell; receiving a second blood fluid portion in the sample analysis system; imaging the first portion in a flow cell; and imaging the second portion in the flow cell, wherein the imaging of the second portion occurs subsequent to the processing of the first portion or at least partially at the same time as the processing of the first portion.

In some embodiments, the imaging of each of the blood fluid portions has an associated imaging time; the processing of each of the blood fluid portions has an associated processing time; and the associated processing times are longer than the associated imaging times.

In some embodiments, the first type of cells comprise white blood cells, and the processing of the first portion comprises staining and incubating the white blood cells of the first portion so as to enhance imageability of the white blood cells.

In some embodiments, each imaging step has a duration of less than about 40 seconds.

In some embodiments, the processing step for the first portion has a duration of more than about 30 seconds.

In some embodiments, the processing step for the first portion further comprises heating the first portion with heating elements at a first processing station.

In some embodiments, the method also includes inputting a first blood fluid sample into the sample analysis system; and separating the first blood fluid sample into the first and second portions, wherein the imaging of the first portion is performed after the imaging of second portion.

In some embodiments, the second portion comprises red blood cells, and the processing of the second portion comprises obtaining a pre-determined blood volume sufficient for imaging the red blood cells.

In some embodiments, the method also includes: after receiving the first and second portions, receiving a third blood fluid portion and a fourth blood fluid portion into the sample analysis system; processing the third portion so as to enhance imageability of the first type of cell; imaging the third portion in the flow cell; imaging the fourth portion in the flow cell; and wherein the imaging of both of the second and fourth portions occur before the imaging of both of the first and third portions.

In some embodiments, the method also includes: after inputting the first blood fluid sample, inputting a second blood fluid sample into the sample analysis system; separating the second blood fluid sample in a third blood fluid portion and a fourth blood fluid portion; and processing the third portion so as to enhance imageability of the first type of cell; wherein at least a portion of the processing of the first portion occurs at a first processing station and wherein at least a portion of the processing of the third portion occurs at a second processing station separate from the first processing station.

In some embodiments, the method also includes: bringing the first portion into contact with a reagent at a first location and subsequently transporting the first portion to the first processing station; and bringing the third portion into contact with the reagent at the first location and subsequently transporting the third portion to the second processing station.

In some embodiments, the method also includes inputting a first blood fluid sample and a second blood fluid sample into the sample analysis system, wherein the first blood fluid sample includes the first portion and the second blood fluid sample includes the second portion; and processing the second portion so as to enhance imageability of the first type of cell; wherein the imaging of the second portion is performed after the imaging of the first portion.

In some embodiments, the second portion comprises white blood cells, and the processing of the second portion comprises staining and incubating the white blood cells so as to enhance imageability of the white blood cells.

In some embodiments, at least part of the processing of the first portion occurs at the same time as at least part of the processing of the second portion.

In some embodiments, processing the first portion includes heating the first portion at a first processing station and processing the second portion includes heating the second portion at a second processing station separate from the first processing station.

In some embodiments, processing the first portion includes contacting the first portion with a reagent at a first reagent location; and wherein processing the second portion includes contacting the second portion with the reagent at the first reagent location.

In some embodiments, a system for imaging a plurality of blood fluid portions includes: a sample fluidic system having: a sample separator valve system, a first blood fluid pathway, a second blood fluid pathway separate from the first blood fluid sample pathway, and a common blood fluid pathway in fluid communication with the first and second blood fluid pathways, wherein the sample separator valve system is in fluid communication with the first and second blood fluid pathways and is configured to deliver a first blood fluid portion containing a first type of cell to the first blood fluid pathway and a second blood fluid portion to the second blood fluid pathway, wherein the first blood fluid pathway comprises a first processing station configured to process the first blood fluid portion so as to enhance imageability of the first type of cell; and a flow cell having a sample port operatively coupled with the common blood fluid pathway such that, when the first and second blood fluid portions are in the sample fluidic system, the first sample portion and the second sample portion are injected into the common pathway to the sample port along the first and second blood fluid pathways, respectively.

In some embodiments, the system also includes a dilution chamber in fluid communication with the valve system and the second blood fluid pathway, such that the valve system delivers the second blood fluid portion to the dilution chamber first before it is being delivered to the second blood fluid pathway In some embodiments, the first process station comprises a heating element to incubate the first blood fluid portion.

In some embodiments, the system also includes temperature sensors coupled to the flow cell or the fluidic system as to produce a temperature reading, and a controller configured to receive the temperature reading from the temperature sensors and to adjust operations of the heating element such that the first blood fluid portion in the first process station is maintained at a desired temperature.

In some embodiments, the system also includes a diluent pump configured to inject a diluent to the second blood fluid pathway as to deliver the second blood fluid portion to the common pathway.

In some embodiments, the system also includes a sample pump configured to inject a fluid to the common pathway so as to deliver the second blood fluid portion from the common pathway to the sample port of the flow cell.

In some embodiment, the system also includes a diluent pump configured to inject a diluent to a substantial part of the second blood fluid pathway and to the dilution chamber, and a vacuum pump configured to evacuate the diluent in the dilution chamber and the substantial part of the second blood fluid pathway.

In some embodiments, the second blood fluid portion comprises the first type of cell, the second blood fluid pathway comprises a second processing station configured to process the second blood fluid portion so as to enhance imageability of the first type of cell, and the first blood fluid portion is directed to the first processing pathway by opening first and second control valves located at the first processing station and closing third and fourth control valves located at the second processing station.

In some embodiments, the second blood fluid portion comprises the first type of cell, the second blood fluid pathway comprises a second process station configured to process the second blood fluid portion so as to enhance imageability of the first type of cell, and the second blood fluid portion is directed to the second blood fluid pathway by closing the first and the second control valves located at the first processing station and opening the third and the fourth control valves located at the second processing station.

In some embodiments, the system also includes a bypass pathway bypassing the first blood fluid pathway, wherein the second blood fluid portion is directed to the second blood fluid pathway through the bypass pathway.

In some embodiments, the second blood fluid portion comprises red blood cells, and the valve system separates the fluidic system into the first blood fluid pathway and the second blood fluid pathway, the second blood fluid pathway including a holding station for holding a pre-determined volume of the second blood fluid portion.

In some embodiments, the holding station comprises a tubing loop an a pair of holding station valves at ends of the tubing loop.

In some embodiments, a method for imaging a plurality of blood fluid portions includes: receiving at least a portion of a first sample into an internal fluidic system of a sample analysis system; after receiving the portion of the first sample into the internal fluidic system, receiving at least a portion of a second sample into the internal fluidic system; after receiving the first and second samples into the internal fluidic system, flowing the portion of the second sample through a flow cell and imaging the portion of the second sample as it flows through the flow cell; after flowing the portion of the second sample through the flow cell, flowing the portion of the first sample through the flow cell.

DETAILED DESCRIPTION OF DRAWINGS

The present disclosure relates to systems and methods for analyzing a fluid sample containing particles. Some embodiments relate to an automated particle imaging system which comprises an analyzer which may be, for example, a visual analyzer, and fluidics systems/sub-systems and methods for directing and staging fluid samples or sample portions for imaging. In some embodiments, the visual analyzer may further comprise a processor to facilitate automated analysis of the images.

The analysis system may be useful, for example, in characterizing particles in biological fluids, such as detecting and quantifying erythrocytes, reticulocytes, nucleated red blood cells, platelets, and white blood cells, including white blood cell differential counting, categorization and sub-categorization and analysis. Other similar uses such as characterizing blood cells or other particles from other fluids are also encompassed by embodiments of the present invention.

(1) Flow Cell, Imaging and Analysis

To facilitate the capacity, speed and effectiveness by which particles such as blood cells are categorized and/or subcategorized, it may be advantageous to provide clear high quality images of the blood cells for automated analysis by a data processing system. In some embodiments, a blood fluid sample or sample portion is introduced into a flowing sheath fluid, and the combined sheath and sample fluids are compressed within a narrowing flow path transition zone that reduces the thickness of the sample ribbon fluid flow. Hence, particles such as cells can be oriented and/or compressed within the blood fluid sample by the surrounding viscous sheath fluid, for example in combination with a geometric focusing effect provided by a narrowing transition zone. Similarly, internal features within blood cells may be, in some non-limiting embodiments, aligned and oriented as a result of a viscosity differential between the sample fluid and the sheath fluid, for example in combination with a geometric focusing effect provided by a narrowing transition zone. Arrangements of the blood cells such as these may facilitate obtaining high quality images of the blood cells for analysis by the data processing system.

Figure 1:
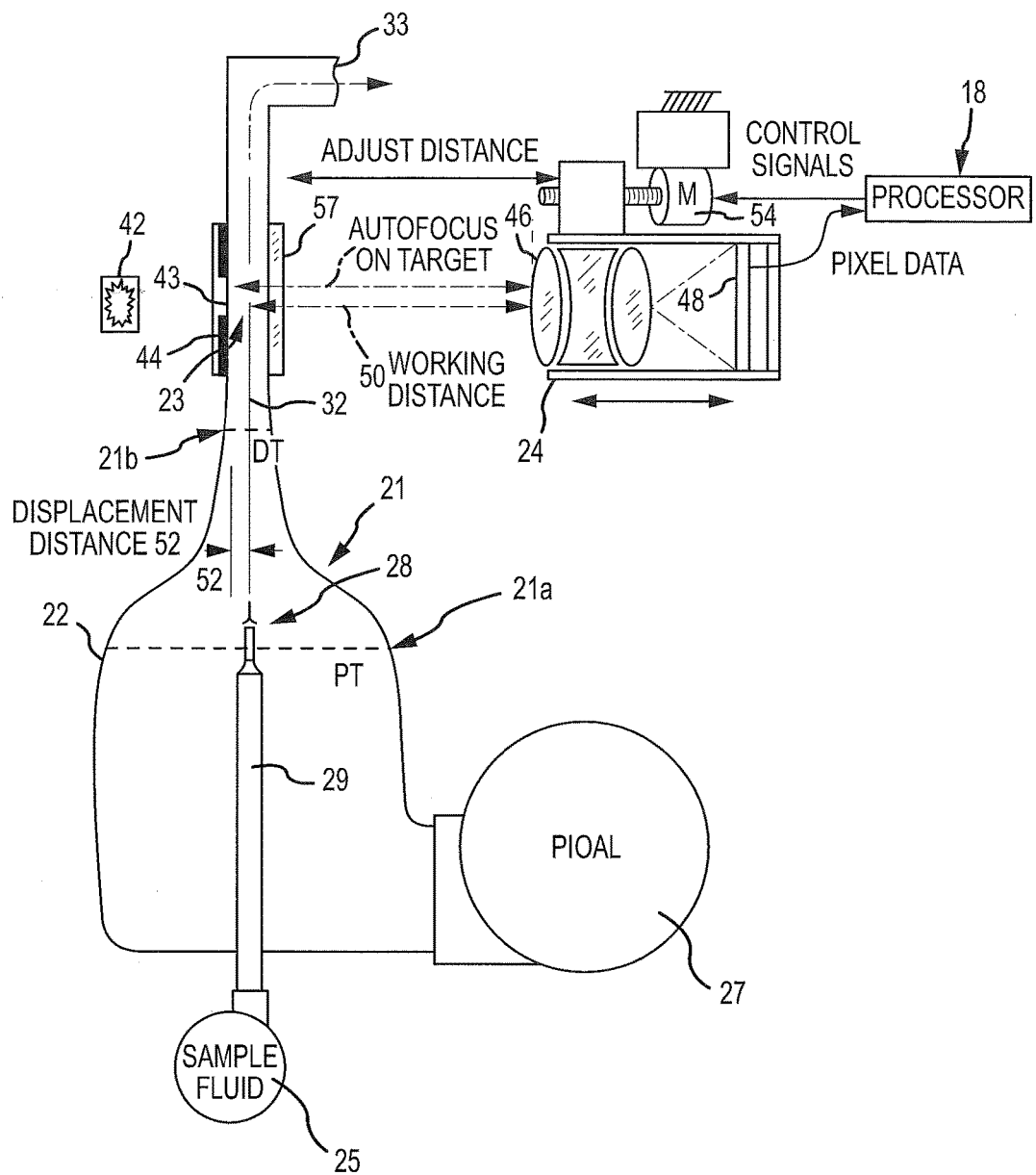
FIG. 1 is a schematic illustration, partly in section and not to scale, showing operational aspects of an exemplary flow cell, autofocus system and high optical resolution imaging device for sample image analysis using digital image processing.

Turning now to the drawings, FIG. 1 schematically shows a flow cell 22 for conveying a sample fluid or fluid portion through a viewing zone 23 of a high optical resolution imaging device 24 in a configuration for imaging microscopic particles in a sample flow stream 32 using digital image processing. Flow cell 22 is coupled to a source 25 of sample fluid or sample portions, some or all of which may have been subjected to processing, such as contact with a particle contrast agent composition and heating. Flow cell 22 is also coupled to one or more sources 27 of a particle and/or intracellular organelle alignment liquid (PIOAL) or other type of sheath fluid, which may be in some instances a clear glycerol solution having a viscosity that is greater than the viscosity of the sample fluid.

In FIG. 1, the sample fluid is injected through a flattened opening at a distal end 28 of a sample feed tube 29, and into the interior of the flow cell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by syringe or other types of precision metering pumps that move the PIOAL with the injected sample fluid along a flow path that narrows substantially. The PIOAL envelopes and compresses the sample fluid in the zone 21 where the flow path narrows. Hence, the decrease in flow path thickness at zone 21 can contribute to a geometric focusing of the sample stream 32. The sample fluid ribbon 32 is enveloped and carried along with the PIOAL downstream of the narrowing zone 21, passing in front of, or otherwise through, the viewing zone 23 of the high optical resolution imaging device 24 where images are collected, for example, using a CCD 48. Processor 18 may receive, as input, pixel data from CCD 48. The sample fluid ribbon flows together with the PIOAL to a discharge or waste 33.

As shown in FIG. 1, the narrowing zone 21 may have a proximal flow path portion 21a having a proximal thickness PT and a distal flow path portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid may enter the PIOAL envelope as the PIOAL stream is compressed by the zone 21.

According to some embodiments, the system may operate to hydro-focus the sample fluid ribbon 32. The term hydro-focus or hydro-focusing may refer to in some instances (while not being limited to) a focusing effect which is influenced by a viscosity difference between the sheath and sample fluids, a geometric narrowing transition zone of the flow cell, and a velocity difference between the sheath and sample fluids. Hydrodynamic flow may result from the velocity difference between the sample and sheath fluid streams, which affects the flow ribbon thickness and shape.

Figure 5:
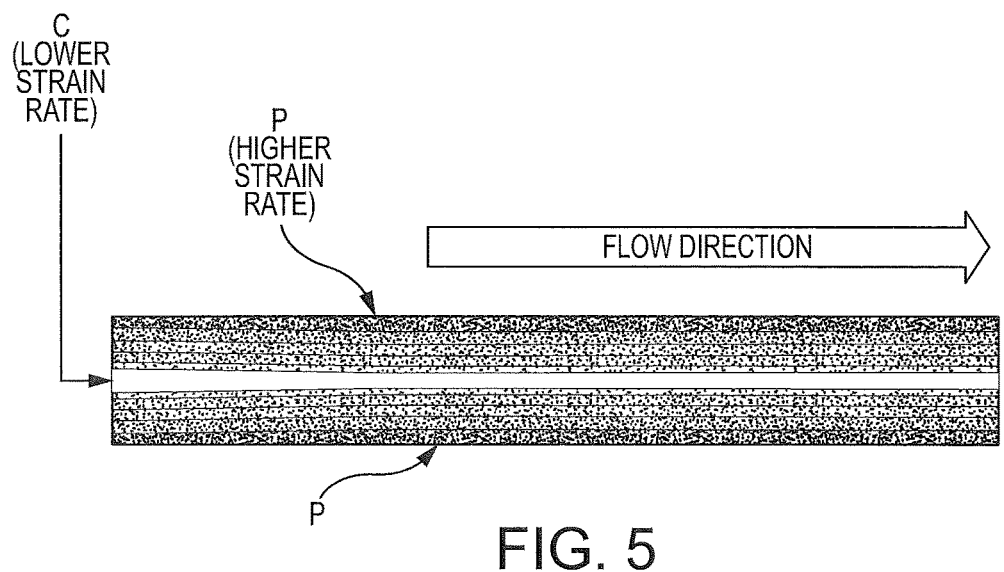
FIGS. 5 and 6 illustrate examples of flow stream strain rates.
Figure 6:
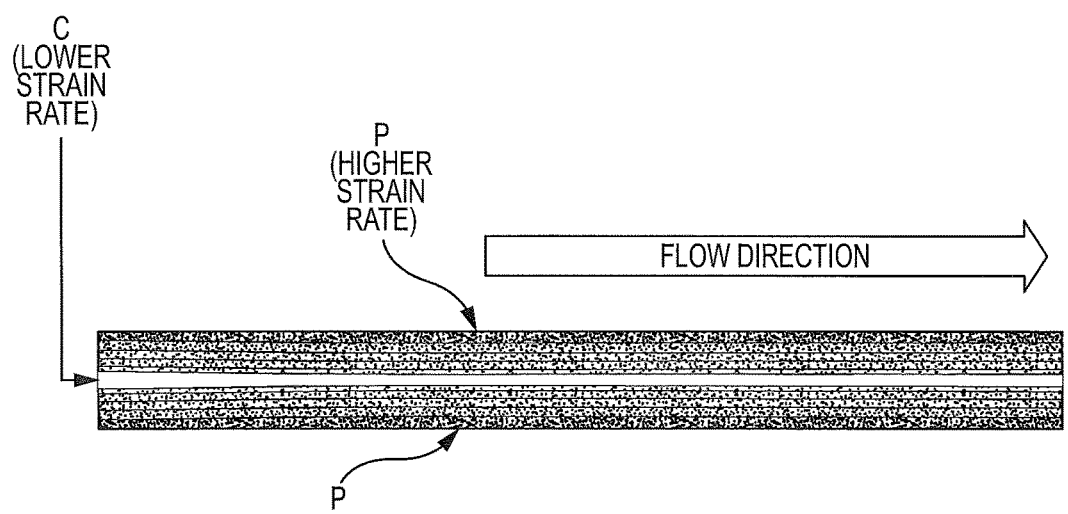

FIGS. 5 and 6 depict aspects of shear strain rate values for certain flow conditions in a flow cell according to embodiments of the present invention. In each of these drawings, a 30% glycerol sheath fluid is used. In some cases, the viscosity can have a value of $2.45 \times 10^{-3}$. A shear stress value can be equal to the product obtained by multiplying a viscosity value with a strain rate value. With regard to FIG. 5, the sample can have a flow rate of 0.3 μL/sec and the sheath fluid can have a flow rate of 21 μL/sec. With regard to FIG. 6, the sample can have a flow rate of 1 μL/sec and the sheath fluid can have a flow rate of 70 μL/sec. In each of these figures, it can be seen that the flow presents a lower strain value toward the center (C) and a higher strain value toward the periphery (P). Such strain values can correspond to an asymmetric flow cell configuration, in some embodiments.

As depicted in FIG. 5, according to some embodiments, the lower strain rate toward the center (C) portion of the flow stream can have a value of about 500 (1/s) or lower and the higher strain rate toward the periphery (P) of the flow stream can have a value of about 3000 (1/s) or higher. As depicted in FIG. 6, according to some embodiments, the lower strain rate toward the center (C) portion of the flow stream can have a value of about 1000 (1/s) or lower and the higher strain rate toward the periphery (P) of the flow stream can have a value of about 9000 (1/s) or higher.

Hence, it can be seen that lower sample and sheath fluid rates (e.g. FIG. 5) correspond to lower strain rates, and higher sample and sheath fluid rates (e.g. FIG. 6) correspond to higher strain rates in this particular example. It is understood that embodiments of the present invention encompass the use of sample and/or sheath fluids corresponding to various viscosity values, various strain rate values, and/or various shear stress values.

The sample fluid ribbon and PIOAL in FIG. 1 flows past a digital high optical resolution imaging device 24 with an objective lens 46 that is directed along an optical axis that intersects the ribbon-shaped sample stream 32. The relative distance between the objective 46 and the flow cell 22 is variable by operation of a motor drive 54, for resolving and collecting a focused digitized image on a photo-sensor array.

Figure 2:
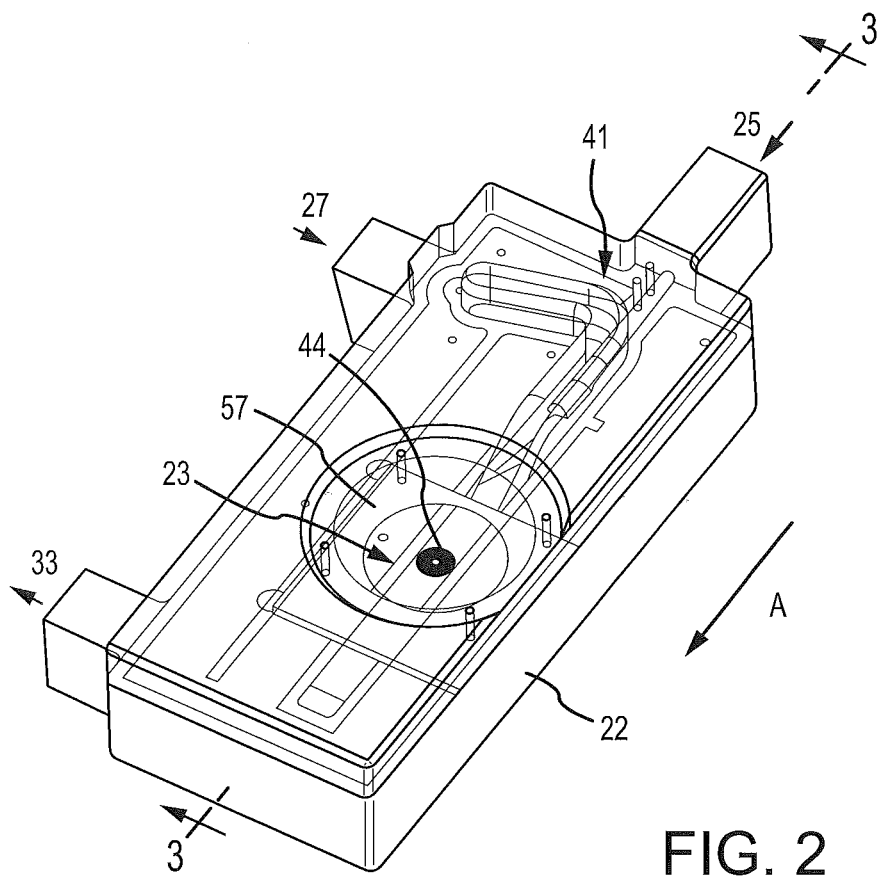
FIG. 2 is a perspective illustration of one example of a flow cell.
Figure 3:
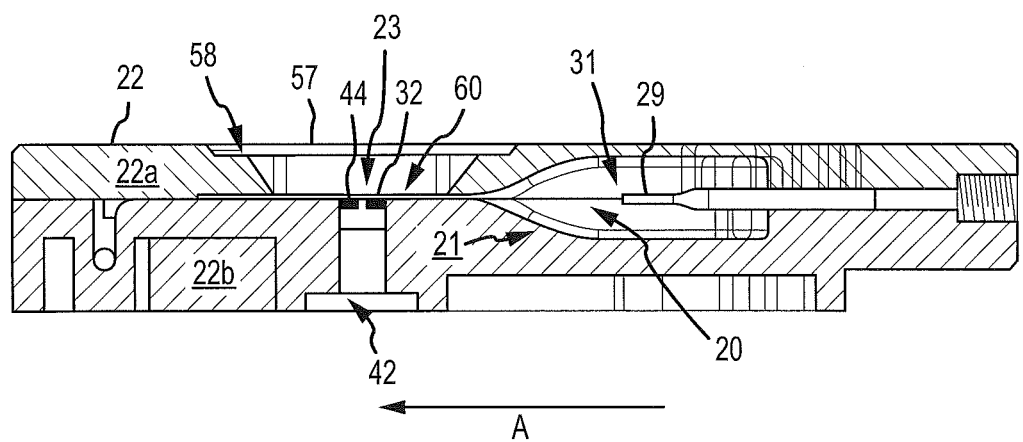
FIG. 3 is a longitudinal median section view along lines 3-3 of the flow cell shown in FIG. 2.

One embodiment of flow cell 22 is further depicted in FIGS. 2 and 3. As shown here, flow cell 22 can be coupled with a sample source 25 and also to a source 27 of PIOAL material. The sample fluid or sample portion is injected into the flow cell 22 via the cannula 29, for example through a distal exit port 31 of the cannula 29. Typically, the PIOAL sheath fluid is not in a laminar flow state as it travels through a curved channel section 41 in the flow cell from the source 27 toward the viewing zone 23. However, the flow cell 22 can be configured so that the PIOAL sheath fluid is or becomes laminar, or presents a flat velocity profile, as it flows past the distal exit port 31 where sample fluid is introduced into the flowing sheath fluid. The sample fluid and the PIOAL can flow along the flow cell 22 in a direction generally indicated by arrow A, and then out of the flow cell 22 via discharge 33. The flow cell 22 defines an internal flow path 20 that narrows symmetrically (e.g. at transition zone 21) in the flow direction A, which may in some instances contribute to a robust and centered flow of the sample stream. The flow cell 22 is configured to direct a flow 32 of the sample enveloped with the PIOAL through a viewing zone 23 in the flow cell, namely behind viewing port 57. Associated with the viewport 57 is an autofocus pattern 44. Flow cell 22 also has a rounded or recessed seat 58 which is configured to accept or receive a microscope objective (not shown).

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flow cell is 1, 2, 3, or 4 seconds, or any range in between any two of those times. In some embodiments the transit time may be less than 4, 3 or 2 seconds.

Figure 3A:
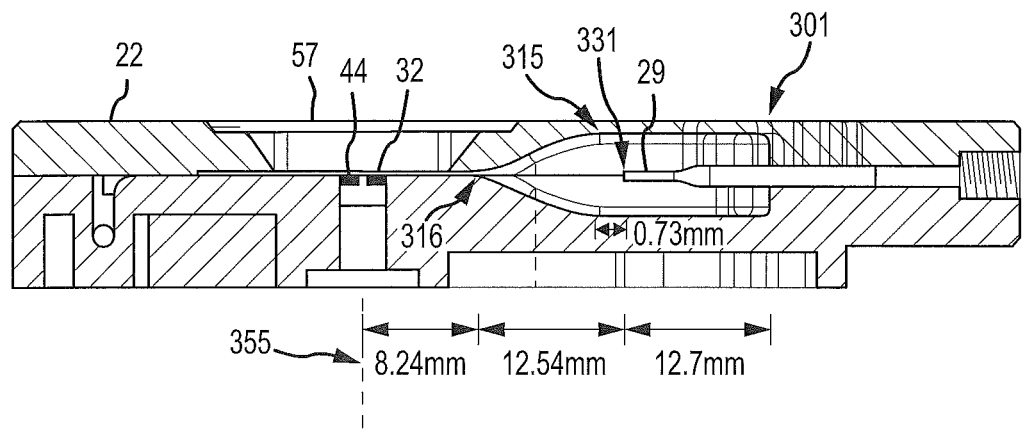
FIGS. 3(a) and 3(b) are section views of other examples of flow cells.
Figure 3B:
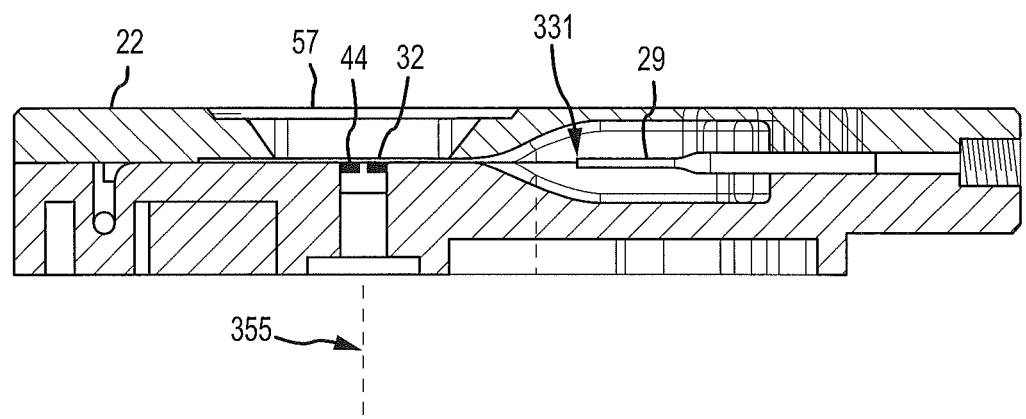

FIG. 3A depicts a flow cell embodiment where a distance between the imaging axis 355 and the distal transition zone portion 316 is about 8.24 mm. A distance between the distal transition zone portion 316 and the cannula exit port 331 is about 12.54 mm. A distance between the cannula exit port 331 and the sheath fluid entrance 301 is about 12.7 mm. A distance between the cannula exit port 331 and a proximal transition zone portion 318 is about 0.73 mm. FIG. 3B depicts aspects of a flow cell embodiment where the cannula exit port has been moved to a more distal location relative transition zone, as compared to the FIG. 3A embodiment. As shown here, the cannula distal end is advanced into the narrowing transition zone of the flow cell, and a distance between the imaging axis 355 and the distal transition zone portion 316 is within a range from about 16 mm to about 26 mm. In some case, the distance between the imaging axis 355 and the distal transition zone portion 316 is about 21 mm.

With returning reference to FIG. 1, the flow cell internal contour (e.g. at transition zone 21) and the PIOAL and sample flow rates may be adjusted in some embodiments such that the sample is formed into a ribbon shaped stream 32. The stream can be approximately as thin as or even thinner than the particles that are enveloped in the ribbon-shaped sample stream. White blood cells may have a diameter around 10 μm, for example. By providing a ribbon-shaped sample stream with a thickness less than 10 μm in some instances, the cells may be oriented when the ribbon-shaped sample stream is stretched by the sheath fluid, or PIOAL. Surprisingly, in some embodiments, stretching of the ribbon-shaped sample stream along a narrowing flow path within PIOAL layers of different viscosity than the ribbon-shaped sample stream, such as higher viscosity, advantageously in some embodiments tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness may be affected by the relative viscosities and flow rates of the sample fluid and the PIOAL. The source 25 of the sample fluid and/or the source 27 of the PIOAL, for example fluidics systems/sub-systems comprising precision displacement pumps, can be configured to provide the sample fluid and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In some embodiments, the PIOAL has a higher linear velocity than the sample and a higher viscosity than the sample, thereby stretching the sample into a flat ribbon in some instances. The PIOAL viscosity can be up to 10 centipoise in some embodiments.

Referring also to FIGS. 2 and 3, the internal flow path of the flow cell narrows downstream of the point of injection of the ribbon-shaped sample stream into the PIOAL, to produce a ribbon-shaped sample stream thickness, for example, up to 7 µm, and/or the internal flow path produces a ribbon-shaped sample stream width of 500-3,000 µm. In some embodiments, such as depicted in FIG. 1, the internal flow path of the flow cell begins a narrowing transition zone upstream of the point of injection of the sample stream into the PIOAL.

In some embodiments, the internal flow path narrows to produce a ribbon-shaped sample stream thickness of 2-4 µm in thickness, and/or the internal flow path results in the ribbon-shaped sample stream of 2000 µm in width. These dimensions may be particularly useful for hematology in some instances. The thickness of the stream in this case is less than the diameter of some particles, such as red blood cells in their relaxed state. Accordingly, those particles may in some uses become reoriented to face their wider a dimension to the imaging axis, which may be helpful in revealing distinguishing characteristics.

In some embodiments, the linear velocity of the ribbon-shaped sample stream can be limited sufficiently to prevent motion blurring of the digitized image at the image exposure time of the photo-sensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

Figure 4:
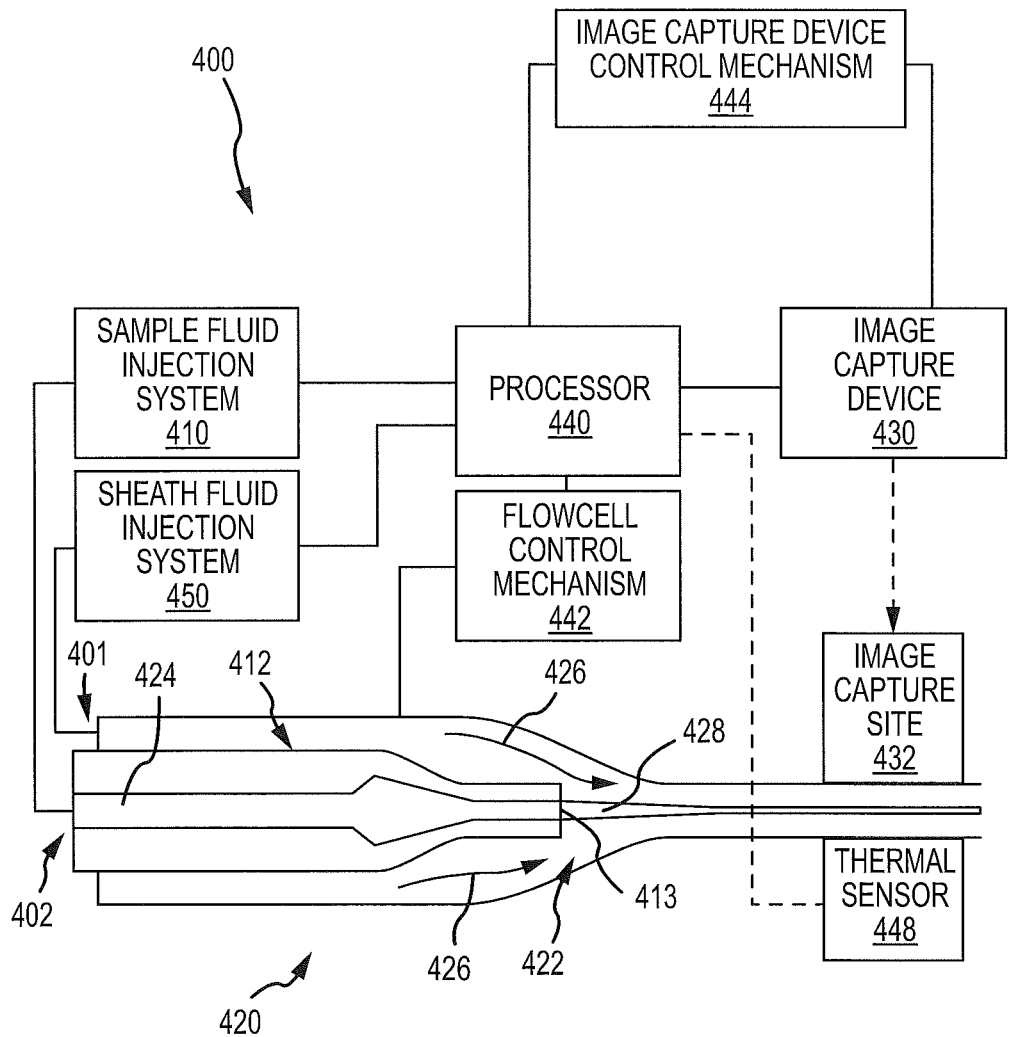
FIG. 4 illustrates aspects of another example of an imaging system.

FIG. 4 depicts another embodiment of a system 400 for imaging particles in a blood fluid sample, samples, and/or sample portions. As shown here, system 400 includes a sample fluid injection system 410, a flow cell 420, an image capture device 430, and a processor 440. The flow cell 420 provides a flow path 422 that transmits a flow of the sheath fluid (such as a PIOAL), optionally in combination with the sample fluid. According to some embodiments, the sample fluid injection system 410 can include or be coupled with a cannula or tube 412. The sample fluid injection system 410 can be in fluid communication with the flow path 422 (e.g. via sample fluid entrance 402), and can operate to inject sample fluid 424 through a distal exit port 413 of the cannula 412 and into a flowing sheath fluid 426 within the flow cell 420 so as to provide a sample fluid stream 428.

The processor 440 may include or be in operative association with a storage medium having a computer application that, when executed by the processor, is configured to cause the sample fluid injection system 410 to inject sample fluid 424 into the flowing sheath fluid 426. As shown here, sheath fluid 426 can be introduced into the flow cell 420 by a sheath fluid injection system 450 (e.g. via sheath fluid entrance 401). In some embodiments, the processor 440 may include or be in operative association with a storage medium having a computer application that, when executed by the processor, is configured to cause the sheath fluid injection system 450 to inject sheath fluid 426 into the flow cell 420.

The processor 440 may be coupled with the sample fluid injector system 410, the image capture device 430, and optionally the sheath fluid injection system 450. The processor 440 may be configured to terminate injection of a first sample fluid (or a first portion of a sample) into the flowing sheath fluid 426 and begin injection of a second sample fluid (or a second portion of the sample) into the flowing sheath fluid 426 such that sample fluid transients are initiated. For example, the processor 440 may include or be in operative association with a storage medium having a computer application that, when executed by the processor, is configured to cause the sample fluid injection system 410 to inject the second sample fluid into the flowing sheath fluid 426 such that sample fluid transients are initiated.

In some embodiments, the processor 440 may be configured to initiate capture of an image or images of a second plurality of the particles from the second sample fluid at the image capture site 432 of the flow cell 420 after the sample fluid transients and within 4 seconds of the imaging of a first plurality of particles from a first sample. For example, the processor 440 may include or be in operative association with a storage medium having a computer application that, when executed by the processor, is configured to cause the image capture device 430 to initiate capture of an image or images of a second plurality of the particles from the second sample fluid at the image capture site 432 of the flow cell 420 after the sample fluid transients and within four seconds of the imaging of the first plurality the particles. In other embodiments, the system may be configured to operate with other time periods separating imaging of the first and second sample fluids, which may or may not involve sample fluid transients.

Any of a variety of hematology or blood particle analysis techniques can be performed using images of sample fluid or sample fluid portions flowing through the flow cell. Often, image analysis can involve determining certain cell or particle parameters, or measuring, detecting, or evaluating certain cell or particle features. For example, image analysis can involve automated computer processing to evaluate or quantify cell or particle size, cell nucleus features, cell cytoplasm features, intracellular organelle features, and the like. Relatedly, analysis techniques can encompass certain counting or classification methods or diagnostic tests, including white blood cell (WBC) differentials. In some cases, images obtained using the flow cell can support a 5-part WBC differential test. In some cases, images obtained using the flow cell can support a 9-part WBC differential test. Relatedly, with reference to FIG. 4, the processor 440 can include or be in operative association with a storage medium having a computer application that, when executed by the processor, is configured to cause the system 400 to differentiate different types of cells based on images obtained from the image capture device. For example, computer-based diagnostic or testing techniques can be used to differentiate various cells (e.g. neutrophils, lymphocytes, monocytes, eosinophils, basophils, metamyelocytes, myelocytes, promyelocytes, and blasts).

The discrimination of blood cells in a blood sample is an exemplary application for which embodiments of the instant invention are particularly well suited, although not being limited thereto. The sample is prepared by automated techniques and presented to a high optical resolution imaging device as a thin ribbon-shaped sample stream (or a series of two or more portions of a sample) to be imaged periodically while the ribbon-shaped sample stream flows across a field of view. The images of the particles (such as blood cells) can be distinguished from one another, categorized, subcategorized, and counted, using pixel image data programmed processing techniques, either exclusively automatically or with limited human assistance, to identify and count cells or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cells of each distinguished category and/or subcategory in the sample as a whole. The sample used for visual discrimination can be diluted, but the proportions of cells in each category and/or subcategory are represented in the diluted sample, particularly after a number of images have been processed.

The sample may be a biological sample, for example, a body fluid sample comprising white blood cells, including without limitation, blood, serum, bone marrow, lavage fluid, effusions, exudates, cerebrospinal fluid, pleural fluid, peritoneal fluid, and amniotic fluid. In some embodiments, the sample may be a solid tissue sample, e.g., a biopsy sample that has been treated to produce a cell suspension. The sample may also be a suspension obtained from treating a fecal sample. A sample may also be a laboratory or production line sample comprising particles, such as a cell culture sample. The term sample may be used to refer to a sample obtained from a patient or laboratory or any fraction, portion or aliquot thereof. The sample can be diluted, divided into portions, or stained in some processes.

The present disclosure further relates to systems, methods and compositions for combining a complete blood count (CBC) counter with an analyzer, such as a visual analyzer, in order to obtain a CBC and an image based expanded white blood cell differential count and an image based expanded platelet count, thereby extending the effective detection range for counting platelets.

In some aspects, samples are presented, imaged and analyzed in an automated manner. In the case of blood samples, the sample may be substantially diluted with a suitable diluent or saline solution, which reduces the extent to which the view of some cells might be hidden by other cells in an undiluted or less-diluted sample. The cells may be treated with agents that enhance the contrast of some cell aspects, for example using permeabilizing agents to render cell membranes permeable, and histological stains to adhere in and to reveal features, such as granules and the nucleus. In some embodiments it may be desirable to stain an aliquot of the sample for counting and characterizing particles which include reticulocytes, nucleated red blood cells, and platelets, and for white blood cell differential, characterization and analysis. In other embodiments, samples containing red blood cells may be diluted before introduction to the flow cell and imaging.

(2) Fluidics Systems and Methods

The embodiments described above may be incorporated into various automated systems or other systems that process, image, and/or analyze large numbers of fluid samples. In some instances, one concern for such systems is optimizing throughput or efficiency. For example, for some embodiments, including some embodiments specific to blood fluids, it may be desirable for a system to have a throughput of 120 samples (or sample portions) per hour or another relatively high throughput rate, such as 60-180 samples per hour, more than 60 samples per hour, more than 100 samples per hour, or other throughput rates.

In one non-limiting example, a system with a target throughput of 120 samples (or sample portions) per hour may be required to aspirate, process and image (and possibly analyze) a sample (or sample portions) every 30 seconds to achieve the target throughput. In some instances, however, some of the steps may require more than 30 seconds to complete. For example, processing a blood fluid sample in preparation for imaging white blood cells in the sample may require more than 30 seconds to complete (e.g. may require approximately 45 seconds to complete). In such instances, additional measures beyond sequential processing, imaging, and/or analyzing of fluid samples may be beneficial to achieving target throughput rates. The above times and throughput rates are provided by way of example only. Other non-limiting embodiments of the present invention may be directed to fluidics systems and methods used for imaging fluid samples in which a processing step for a sample or sample portion requires or otherwise occupies a time period that is of a length that would prevent achieving a desired throughput rate for the system if all of the samples/sample portions were simply processed and imaged in sequential order in series.

FIGS. 7-12 illustrate various embodiments of staging the processing and imaging of samples/sample portions in accordance with various embodiments of the present invention. It should be understood that while specific times are shown for the stagings reflected in FIGS. 7-12, that these stagings could be implemented for other staged methods where some steps take longer than other steps.

Figure 7:
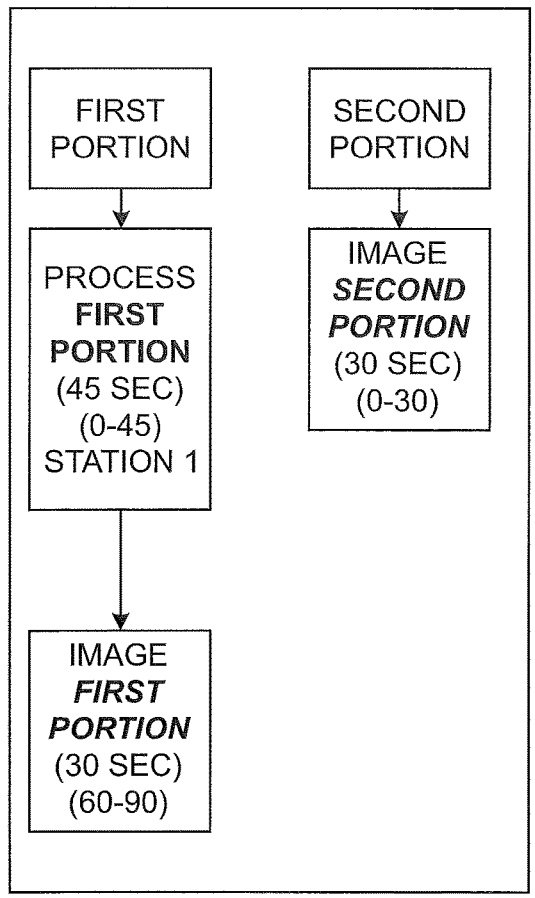
FIGS. 7-12 illustrate examples of timing or staging of the processing and imaging of various fluid samples.

FIG. 7 illustrates an embodiment including a first sample portion and a second sample portion. In this embodiment, the first sample portion is processed during a 45 second time period (during time 0 to time 45) while the second sample portion is imaged during a 30 second time period (during time 0 to time 30), with the first sample portion being imaged during a 30 second time period (during time 60 to time 90) after its processing is complete and after the imaging of the second sample portion is complete. In the embodiments of FIGS. 7-12, imaging steps are illustrated as occurring in a 30 second time period; however, in at least some instances, actual imaging will not occur during the entirety of the 30 second time period, and may require less than 30 seconds, such as approximately 2-3 second, 5 seconds, 20 seconds, or another period of time between 1 and 30 seconds. Imaging may require (or otherwise occupy) different amounts of time for the first portion and second portion. For instance, in some embodiments, imaging of a first portion after processing may occupy substantially longer time periods that imaging of a second portion that is not processed in the same manner as the first portion (e.g. fluid sample portions being imaged for white blood cells may require or otherwise occupy more imaging time than fluid sample portions being imaged for red blood cells). It should also be understood that both the 45 and the 30 second time periods illustrated in FIGS. 7-12 are only examples, and that other times are contemplated and within the scope of the present invention.

In one example consistent with the embodiment of FIG. 7 (and other figures), the first sample portion may be a portion of a blood fluid sample that is processed to facilitate or enhance imaging of white blood cells. Processing may include mixing or otherwise contacting the first sample portion with a reagent that stains the white blood cells and lyses the red blood cells in the first sample portion. Processing may also include incubating the first sample portion after contact with the reagent by the application of heat. While FIG. 7 indicates that the processing of the first portion occurs at a single station, in some embodiments, including some embodiments described further below, processing may occur at multiple locations. For example, the first sample portion may mix with the reagent in a mixing chamber and then move to a separate incubation station to complete its processing.

In one example consistent with the embodiment of FIG. 7 (and other figures), the second sample portion may be another portion of the blood fluid sample discussed immediately above, with this portion being used for imaging of red blood cells in the sample. In some instances it is not necessary to extensively process the second sample portion or process it at all. In some instances, the second sample may be diluted prior to imaging, but is not contacted with reagents, otherwise processed, or processed in a manner that requires any significant amount of time.

In some embodiments, processing of a first cell type (e.g. staining and incubating a portion of a blood fluid sample to enhance imageability of white blood cells in the sample portion) may require or otherwise occupy longer time segments than time segments required or otherwise occupied by other steps involved in the overall imaging process. For instance, in some embodiments, processing a portion of a blood fluid sample may require or otherwise occupy more time than imaging of that sample portion, alone or in combination with other processing steps described further below. In these and other embodiments, processing a portion of a blood fluid sample to enhance imageability of certain types of cells in that sample portion may require or otherwise occupy more time than an entire process requires or otherwise occupies for other portions of blood fluid samples, such as sample portions that are not processed to enhance imageability of certain cell types in the sample portion.

While not specifically shown in FIG. 7, it will be apparent to those of ordinary skill in the art that the staging illustrated in FIG. 7 (and other figures) can be repeated multiple times for multiple samples/sample portions.

Figure 8:
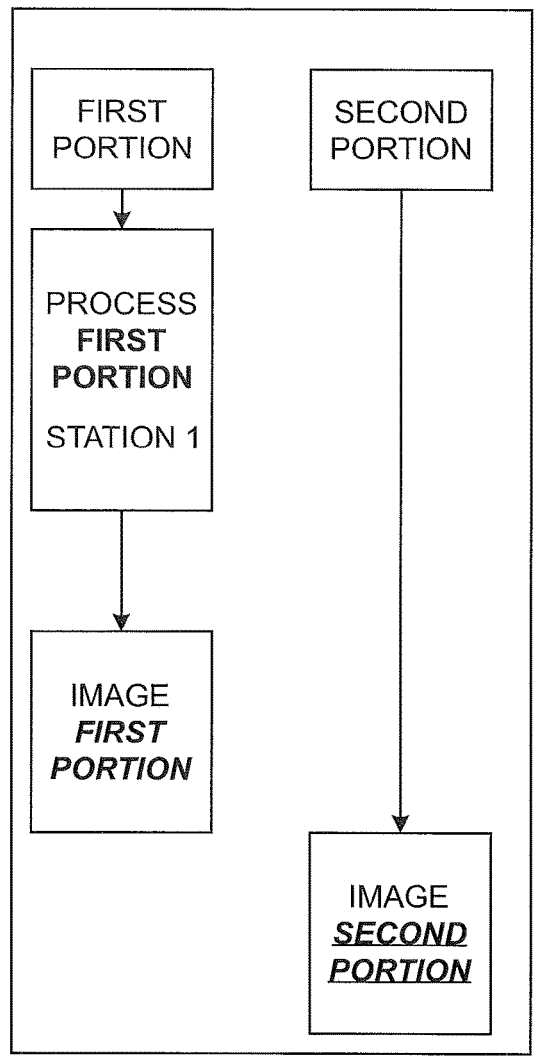

FIG. 8 illustrates an embodiment that also includes a first sample portion and a second sample portion; however, in this embodiment, the second sample portion is imaged after both processing and imaging of the first sample portion is completed.

Figure 9:
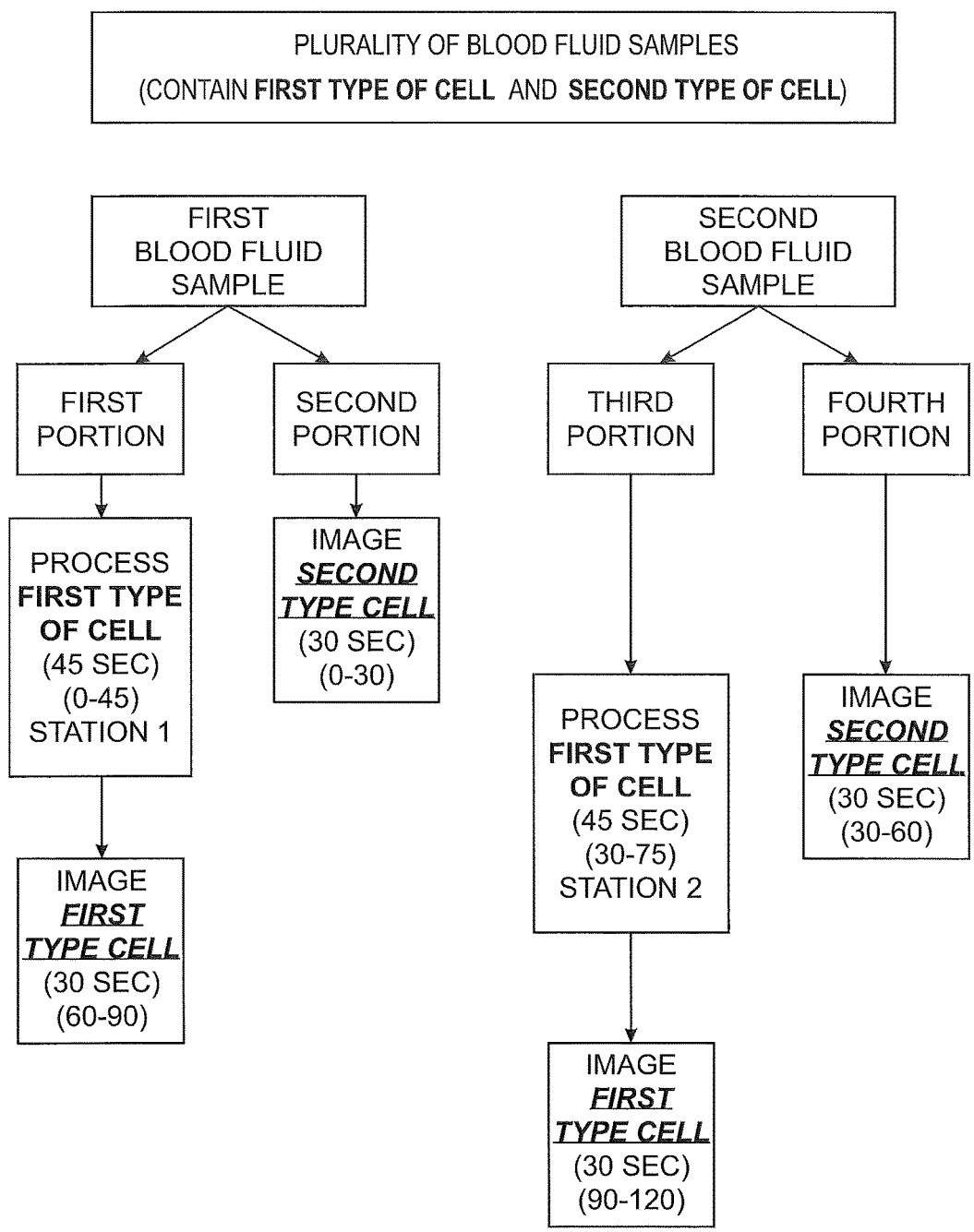

FIG. 9 illustrates an embodiment including a first blood fluid sample and a second blood fluid sample, the blood fluid samples including multiple cell types (e.g. red blood cells, white blood cells, and possibly other cell types or particles). The first blood fluid sample is separated into a first portion (e.g., in some instances, used for imaging white blood cells in the first sample) and a second portion (e.g., in some instances, used for imaging red blood cells in the first sample). The second blood fluid sample is separated into a third portion (e.g., in some instances, used for imaging white blood cells in the second blood fluid sample) and a fourth portion (e.g., in some instances, used for imaging red blood cells in the second blood fluid sample).

In this embodiment, the first portion is processed during a 45 second time period at time 0 to time 45 (e.g. to lyse red blood cells and stain white blood cells) while the second portion may be imaged during at least a portion of a thirty second time period at time 0 to time 30 (e.g. to image the red blood cells in the second portion). Part of the processing of the third portion (which occurs during a 45 second time period at time 30 to time 75) also occurs while the first portion is processing (the overlap occurring at time 30 to time 45, for approximately 15 seconds). Imaging of the fourth portion (which occurs during at least a portion of a thirty second time period at time 30 to time 60, after the imaging of the second portion) may, in some instances, overlap with both processing of the first and third portions. Imaging of the first portion occurs after the imaging of the second and fourth portions, and may partially overlap with the processing of the third portion. Imaging of the third portion occurs after the first, second and fourth portions have been imaged, and after the first and third portions have been processed.

As shown in FIG. 9, at least a portion of the processing of the first portion of the first blood fluid sample and the third portion of the second blood fluid sample may occur at different processing stations. For instance, in embodiments where the first and third portions are portions of blood fluid samples to be imaged for white blood cells, the processing may include mixing or otherwise contacting the sample portions with a reagent (which may take a relatively short amount of time, e.g. a few seconds), and also include incubating the sample portions through application of heat (which may take a relatively long amount of time, e.g. approximately 45 seconds). In some instances, both the first and third portions may be mixed with reagent at the same mixing chamber (albeit at different times), but be incubated at two separate incubation stations ("station 1" and "station 2" in FIG. 9). In other instances, the first portion may be both mixed and incubated at a separate location from the third portion. In the embodiment of FIG. 9, a sample can be processed and imaged approximately every 30 seconds, even though the processing step requires more than 30 seconds, due to the use of multiple processing stations.

Although not shown explicitly in FIG. 9, the first blood fluid sample may be obtained and separated into the first and second portions prior to the second blood fluid sample being obtained and separated into the third and fourth portions. For instance, in some embodiments, a system may aspirate the first blood fluid sample from a container (e.g. a sample tube) into the system and separate it into the first and second portions, and then, at a later time, aspirate the second blood fluid sample from a second container into the system and separate it into the third and fourth portions. In some instances, samples may be aspirated at approximately the same time interval as imaging of other sample portions are completed. For example, in FIG. 9, the second sample may be aspirated around time 30, approximate the completion of the second portion's imaging.

As illustrated by, for example, the stagings shown in FIG. 9 (and other figures), some embodiments stage the processing and imaging steps for the various samples and sample portions in a non-sequential, interleaved, or out of order manner. For instance, the fourth portion of the second blood fluid sample (which, as mentioned above, may in some instances be a sample that was received in the system after the first sample) may be imaged before the first portion of the first sample, but after the second portion of the first sample, with the imaging steps being interleaved or alternated between the first and second samples, even though the second sample may have been obtained or received into the system after processing of the first sample had already begun.

Figure 10:
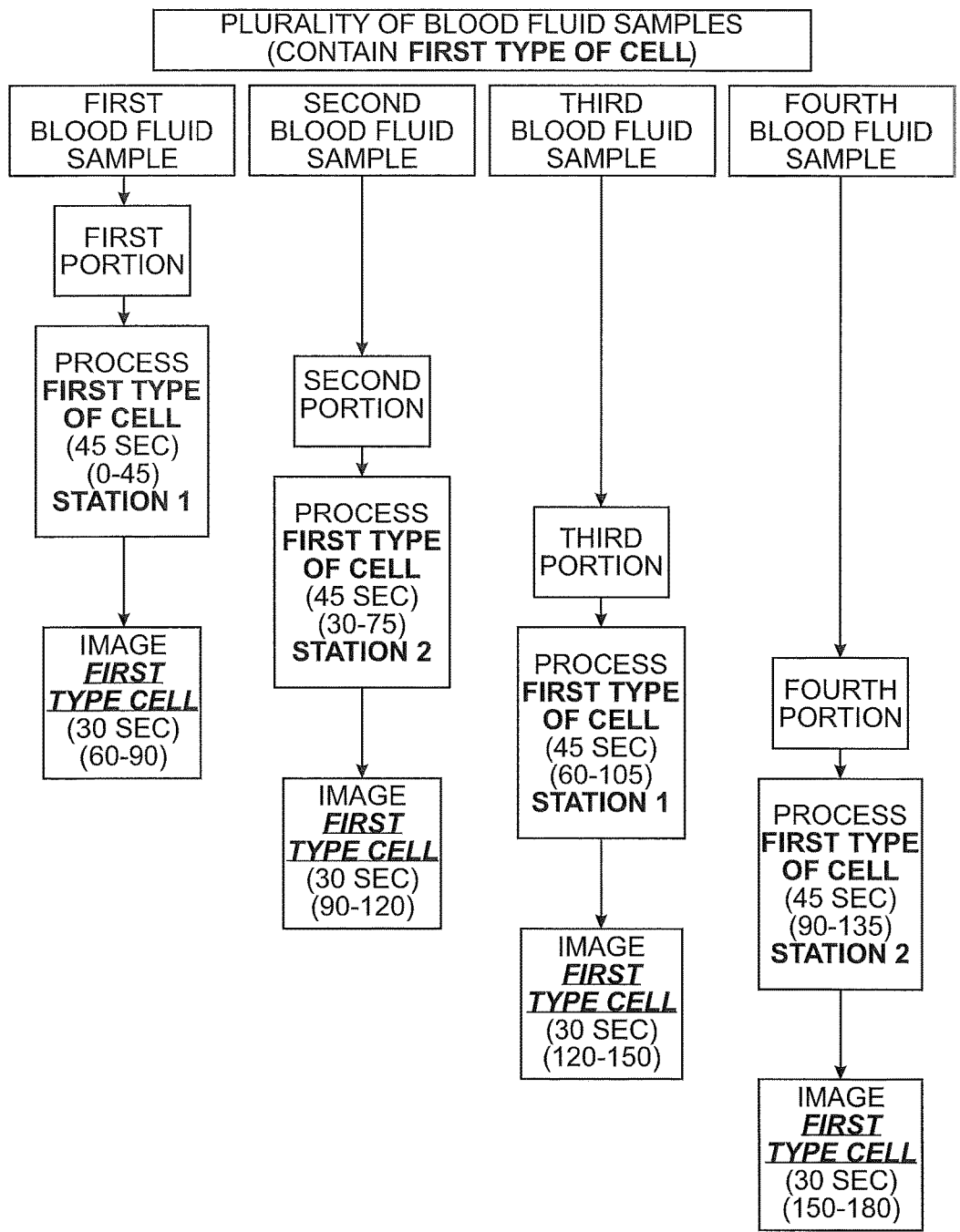

FIG. 10 illustrates an embodiment including first, second, third and fourth blood fluid samples, each sample including at least a first type of cell of interest (e.g. at least white blood cells). In FIG. 10, portions of the four samples are processed and imaged in order, and at least part of the processing (e.g. an incubation step) occurs at either a first station ("station 1" in FIG. 10) or a second, separate station ("station 2" in FIG. 10) such that at least part of the processing can overlap in time or occur simultaneously for multiple sample portions.

Specifically, in the embodiment of FIG. 10, processing of the first and second sample portions overlaps (with the first portion being processed at a first station and the second portion being processed at a second station), processing of the second and third sample portions overlaps (with the third portion being processed at the first station after processing of the first portion is completed), and processing of the third and fourth sample portions overlaps (with the fourth portion being processed at the second station after processing of the second portion is completed). In the embodiment of FIG. 10, a sample can be processed and imaged approximately every 30 seconds, even though the processing step requires more than 30 seconds, due to the use of multiple processing stations.

Figure 11:
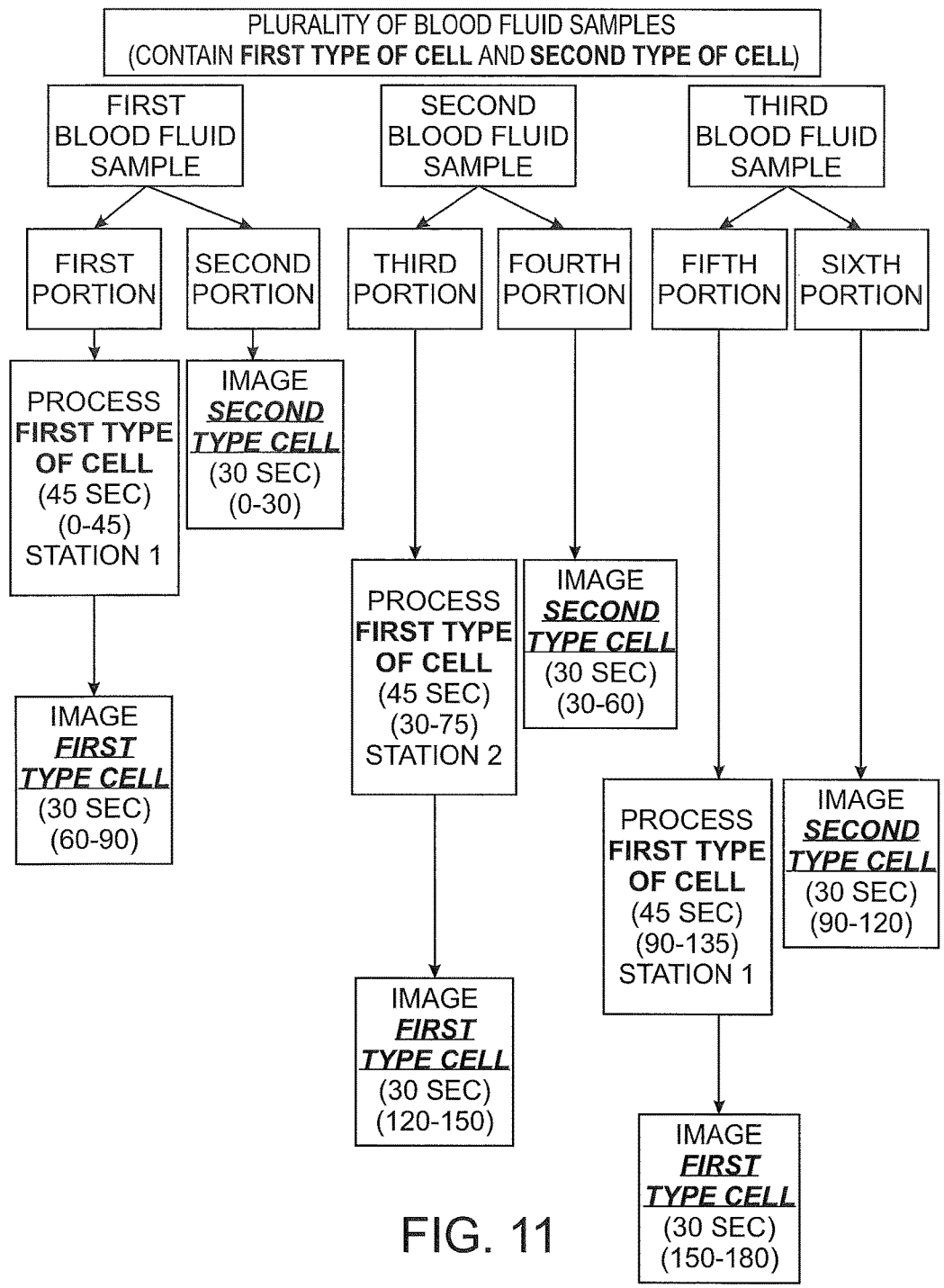
Figure 12:
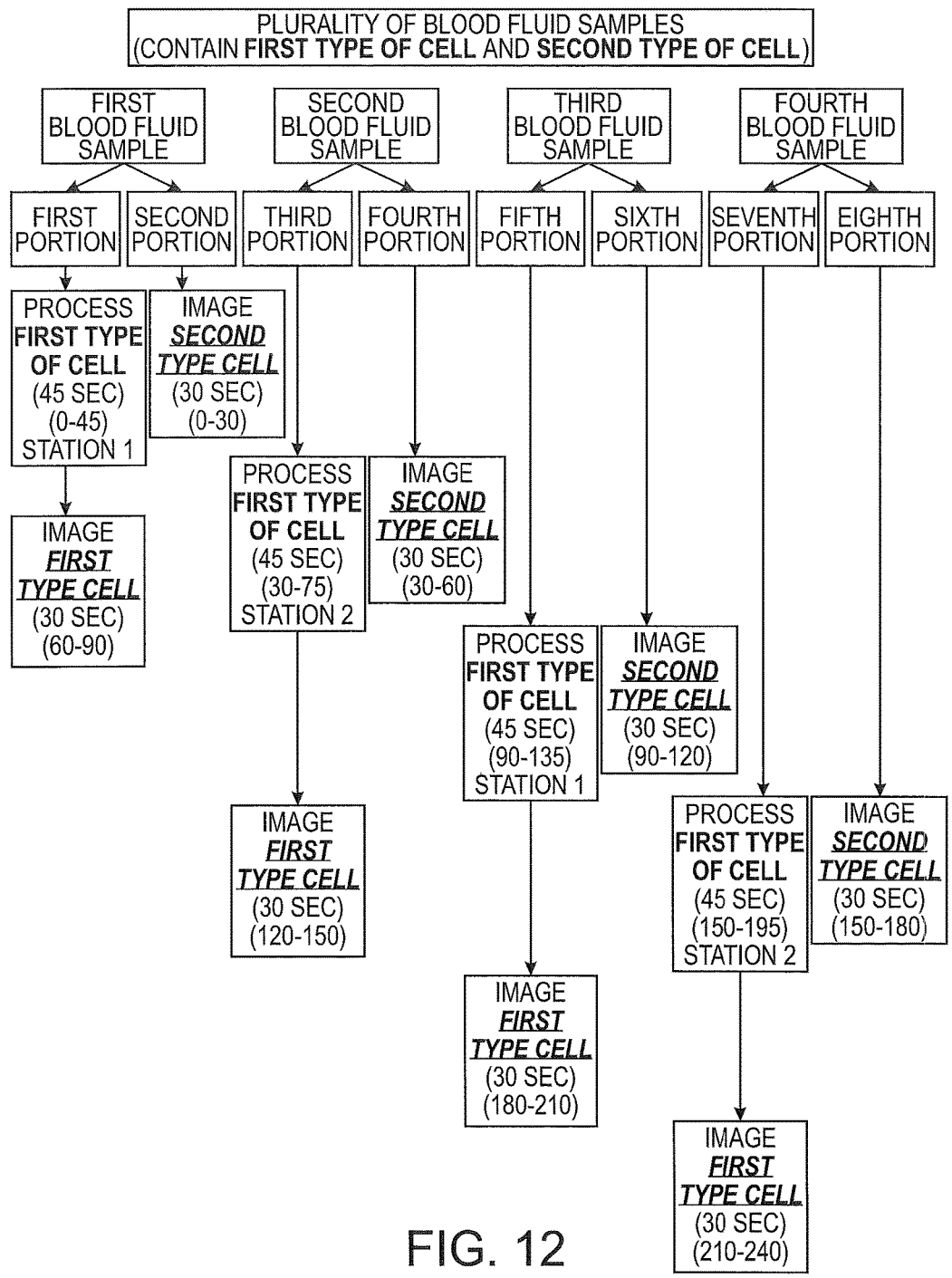

FIG. 11 illustrates an embodiment including first, second, and third blood fluid samples, each containing at least two cell types (e.g. red blood cells and white blood cells), and each separated into two portions (the "first" through "sixth portions" in FIG. 11). As with some of the embodiments discussed above, the imaging steps for the various sample portions are interleaved, such that imaging takes place in the following order: (1) imaging the second type of cell in the first sample; (2) imaging the second type of cell in the second sample; (3) imaging the first type of cell in the first sample; (4) imaging the second type of cell in the third sample; (5) imaging the first type of cell in the second sample; and (6) imaging the first type of cell in the third sample. FIG. 12 is similar to FIG. 11, except that it includes a fourth blood fluid sample in the staging, such that imaging takes place in the following order: (1) imaging the second type of cell in the first sample; (2) imaging the second type of cell in the second sample; (3) imaging the first type of cell in the first sample; (4) imaging the second type of cell in the third sample; (5) imaging the first type of cell in the second sample; (6) imaging the second type of cell in the fourth sample; (7) imaging the first type of cell in the third sample; and (8) imaging the first type of cell in the fourth sample. As with FIGS. 9 and 10, FIGS. 11 and 12 utilize two separate stations for processing a first type of cell.

It should be understood that the specific duration and timing of the steps illustrated in FIGS. 7-12 are only examples, and other durations and timings are possible. As one alternative example, it should be noted that in, for instance, FIGS. 10-12, both "station 1" and "station 2" are not always in use, and thus the specific start, duration, and termination times of the process steps schematically indicated by these figures could be altered without impact on the staging illustrated in these figures. As one specific example, in FIG. 10, "station 1" is shown as in use at time 0 to time 45 and time 60 to time 105, but not at time 46 to time 59, and, as such, adjustments to the start, duration, and termination of the processes occurring at "station 1" are possible without affecting the overall staging shown in FIG. 10 and while still providing for an imaging step to be completed every 30 seconds.

FIGS. 13(a)-13(m) illustrate one embodiment of a fluidics system configured to implement at least some of the staging methods illustrated in FIGS. 7-12, including the multiple station embodiments illustrated in FIGS. 9-12. In some embodiments, the fluidics system illustrated in FIGS. 13(a)-13(m) functions (in whole or part) as the sample and PIOAL sources 25, 27 shown in FIG. 1 and described above. In some embodiments, the fluidics system illustrated in FIGS. 13(a)-13(m) functions (in whole or part) as the sample and sheath fluids injection systems 410, 450 illustrated in FIG. 4.

FIGS. 13(a)-13(m) illustrate the progression of several fluid sample portions through the system to a flow cell 1302, including sample portions labeled WBC 1, RBC 1, WBC 2, and RBC 2 (some of which are not introduced until later figures in FIGS. 13(a)-13(m)). In the non-limiting example illustrated in FIGS. 13(a)-13(m), sample portions WBC 1 and WBC 2 represent portions of blood fluid samples that will be imaged at flow cell 1302 for white blood cells, and sample portions RBC 1 and RBC 2 represent corresponding portions of the blood fluid samples that will be imaged at flow cell 1302 for red blood cells. In other words, in the particular embodiment shown, RBC 1 and WBC 1 are from a single blood sample.

In FIGS. 13(a)-13(m), fluid sample portions are introduced into the system at sample separator 1304. In the particular embodiment shown, sample separator 1304 is a shear valve configured to separate sample portions from a blood fluid sample aspirated from a tube or other container. The shear valve may be configured to separate specific, pre-determined volumes of the fluid sample portions from the aspirated sample. In one example, one aspiration from a container will fill several (e.g. two) tubing loops associated with the shear valve with fluid sample portions. While not shown, the system may be configured to aspirate or otherwise obtain samples from large numbers of sample tubes, which may be held in racks or other bulk holding devices. In some embodiments, a rack transport system may move sample tubes sequentially into proximity with a probe that aspirates a sample from a tube, for subsequent transport to the shear valve described above. In these or other embodiments, the system may also include a manual input or other mechanism for introducing samples into the system out of order with the sample tubes held in racks.

A hematology system according to embodiments of the present invention can process a blood sample having a volume of about 150 µL. The aspirated blood volume can be about 120-150 µL. In some cases, the minimum available blood volume in the sample tube is about 500 µL for an automatic sampling mode and about 250 µL for manual sampling mode.

Figure 13A:
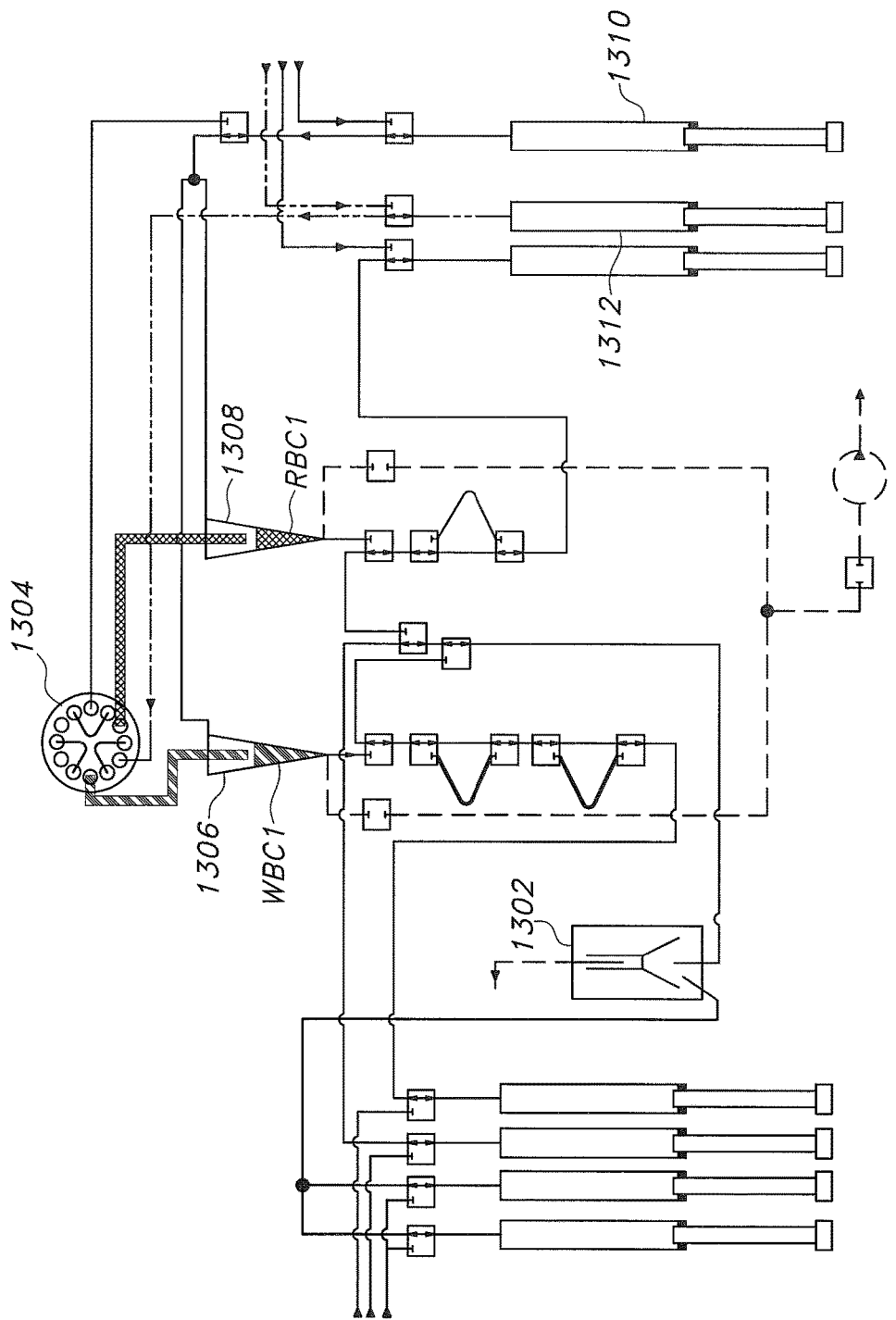
FIGS. 13(a)-13(m) illustrate an example of a fluidics system with different flow sequences of an automated imaging system.
Figure 13B:
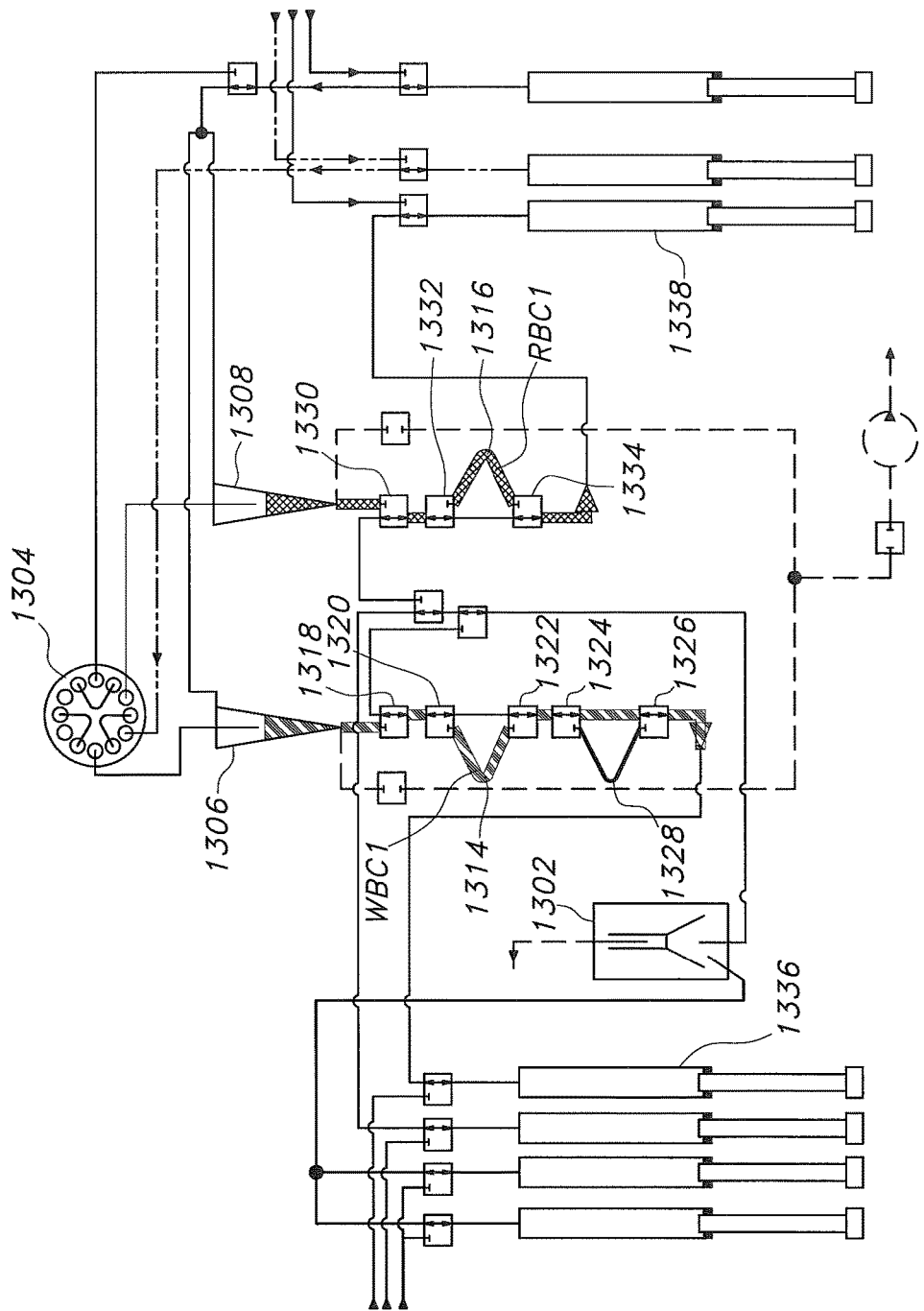
Figure 13C:
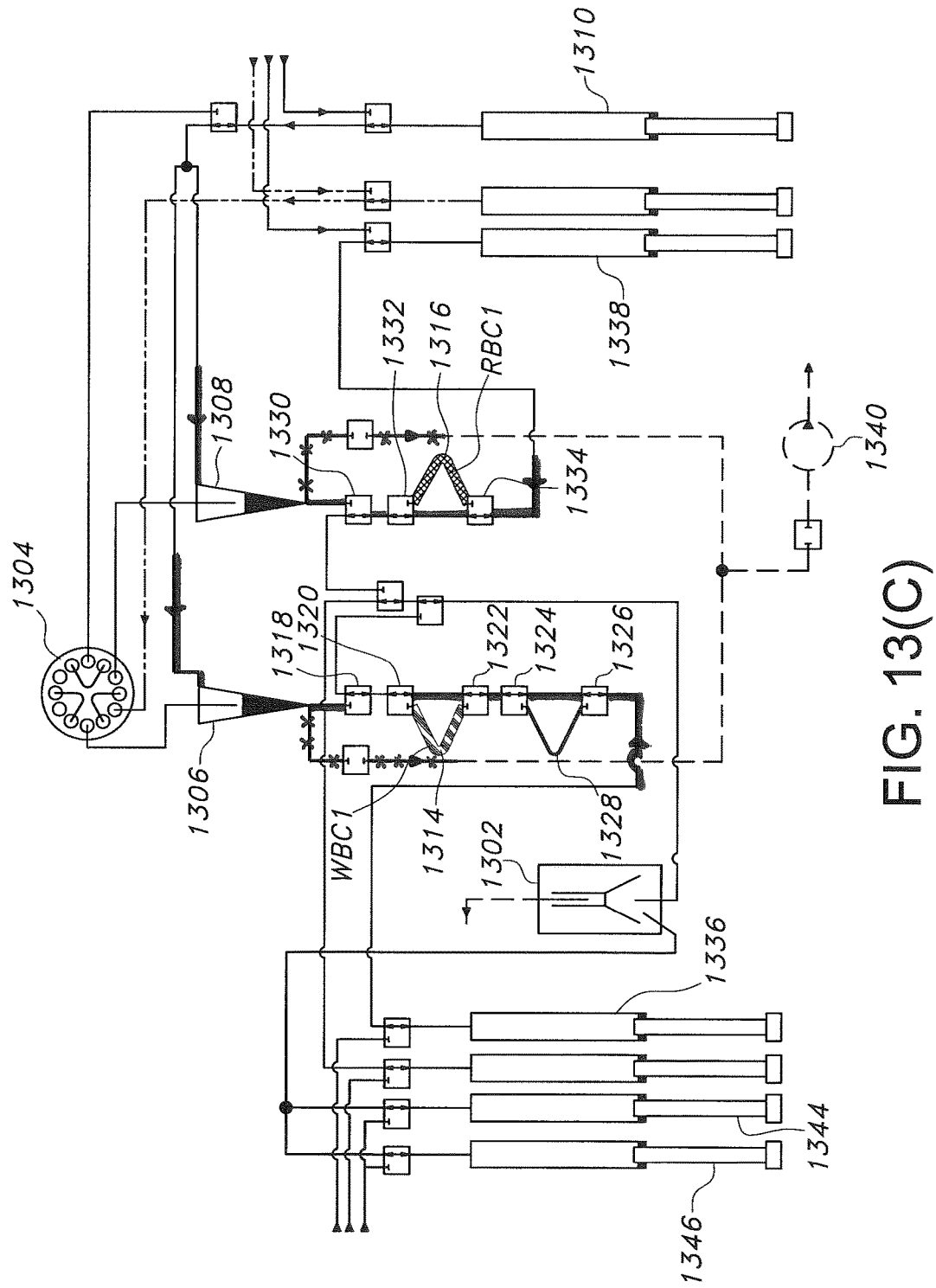

Beginning at FIG. 13(a), fluid sample portions WBC 1 (shown as a backwards diagonal crosshatch line) and RBC 1 (shown as diagonal crosshatch line) are first received from sample separator 1304 at mixing chambers 1306 and 1308 respectively. Sample separator 1304 may be configured to provide a specific and defined volume of the fluid sample portions into the mixing chambers. At mixing chamber 1306, WBC 1 mixes or is otherwise contacted with a diluent and a reagent configured to lyse red blood cells and stain white blood cells in the fluid sample portion. At mixing chamber 1308, RBC 1 mixes with a diluent, but, at least in this particular embodiment, is not otherwise treated. Pump 1310 may pump diluent through the sample separator 1304 and into both of the mixing chambers 1306, 1308. In the particular embodiment shown, pump 1310 is a syringe pump (as well as some of the other pumps described below), which may periodically refill by drawing diluent from a bulk container holding a large volume of diluent (not shown). Pump 1312 (which may also be a syringe pump that draws reagent from a bulk container) may pump reagent through sample separator 1304 and into mixing chamber 1306. In some embodiments, pumps 1310, 1312 may pump diluent and reagent into the appropriate mixing chambers via the sample separator 1304 (rather than directly into the mixing chambers 1306, 1308) in order to supply a specific and defined volumes of the diluent and/or reagent into the approximate mixing chambers. In some embodiments, this will also move fluid sample portions WBC 1 and RBC 1 from the sample separator 1304 into the mixing chambers

1306 and 1308. In other embodiments, diluent and/or reagent may directly pumped into the mixing chambers or introduced into the mixing chambers in another manner, in pre-defined volumes, for pre-defined times, or in other pre-defined or non-pre-defined manners. In some embodiments, mixing may take five second or less, or, in some embodiments approximately two seconds.

As shown in FIG. 13(*b*), after mixing, fluid sample portion WBC 1 is directed from the mixing chamber 1306 into first incubation station 1314 and RBC 1 is directed from the mixing chamber 1308 into holding station 1316. In the particular embodiment shown, WBC 1 passes through fluidics circuitry including valves 1318, 1320, 1322, 1324, 1326, which are configured such that WBC 1 will flow into the first incubation station 1314, and, in some instances, a portion of WBC 1 may flow out of the first incubation station 1314 and may flow in bypass past a second incubation station 1328. Valves 1318, 1320, 1322, 1324, 1326 may be multi-port valves that may be actuated (such as by a processor-based control system) to direct fluids passing through them to different exit ports of the valves, depending on the particular configuration of the valve at the time. Thus, at the time segment illustrated in the particular example of FIG. 13(*b*), valves 1320 and 1322 are configured to allow fluid to enter first incubation station 1314, rather than bypassing it, and valves 1324 and 1326 are configured to prevent fluid from entering second incubation station 1328, and to instead flow through a bypass line past it. The holding station 1316 holding RBC 1 in FIG. 13(*b*) is proximate valves 1330, 1332, 1334. At the time segment illustrated in the particular example of FIG. 13(*b*), valves 1332 and 1334 are configured to allow fluid to enter the holding station 1316, rather than flowing through a bypass line past it.

In the particular embodiment shown, pumps 1336, 1338 may be used to draw fluid sample portions WBC 1 and RBC 1 into the portions of the fluidics circuitry illustrated in FIG. 13(*b*).

In the particular embodiment shown, the volume of WBC 1 and RBC 1 (including, in some instances, the volume of WBC 1 and RBC 1 including the mixed in diluent and/or reagent) is greater than the fluid capacity of the first incubation station 1314 and the holding station 1316 respectively, and the system is configured such that, as shown in FIG. 13(*b*), some of WBC 1 and RBC 1 remain in the valves and/or passageways outside either end of the first incubation station 1314 and the holding station 1316 respectively after they have been completely loaded. In some, although not necessarily all, embodiments, this may facilitate ensuring that the fluid held within the first incubation station 1314 and the holding station 1316 is entirely composed of mixed WBC 1 and RBC 1 respectively, and of a specific, defined, and/or repeatable volume. In some, although not necessarily all, embodiments, this may also facilitate ensuring that any air that may be present and the beginning or the end of the sample drawn from the mixing chamber will not be present in the first incubation station 1314 or the holding station 1316.

In some embodiments, loading of WBC 1 into the first incubation station 1314 and loading of RBC 1 into the holding station 1316 may take five second or less, or, in some embodiments approximately three seconds.

Incubation stations 1314 and 1328 may be proximate one or more heating elements (not shown) configured to apply heat to fluids held within the incubation stations. In some instances, one or more temperature sensors or other functionality may be included to, directly or indirectly, measure temperature or otherwise regulate temperature at the incubation stations. In some instances, incubation stations 1314 and 1328 and/or associated heating elements may be insulated to reduce heating of other components or areas of the system. In some instances, WBC 1 and other sample portions processed to enhance imageability of white blood cells may be incubated at one of the incubation stations 1314 or 1328 for approximately 45 seconds.

In some instances, WBC 1 and other sample portions processed to enhance imageability of white blood cells may be incubated at one of the incubation stations 1314 or 1328 for longer time segments than those sample portions require or otherwise occupy for other steps illustrated in FIGS. 13(*a*)-13(*m*) (individually or in total). In some instances, WBC 1 and other sample portions processed to enhance imageability of white blood cells may be incubated for longer time segments than a desired throughput rate of the system (e.g. incubated for 45 seconds with a desired throughput rate of 1 sample portion (or sample) every 30 seconds). In the embodiment shown, WBC 1 may be incubated at incubation stations 1314 for a longer time than RBC 1 requires or otherwise occupies to complete all the steps illustrated in FIGS. 13(*a*)-13(*f*). In the embodiment shown, WBC 1 may be incubated at incubation stations 1314 for a longer time than both RBC 1 and RBC 2 require or otherwise occupy to complete all the steps illustrated in FIGS. 13(*a*)-13(*m*).

In some embodiments, incubation stations 1314, 1328 and holding station 1316 may be tubing loops that are sized to hold a sufficient volume of a fluid sample portion for imaging at flow cell 1302. In other embodiments, other components or configurations may be employed to hold sufficient and/or pre-determined volumes of fluid samples. In still other embodiments, distinct stations may not be necessary, and the system may otherwise be configured to process or direct fluid sample portions to flow cell 1302 without the need for segregated or distinct stations.

Turning to FIG. 13(*c*), after loading, portions of the fluidics circuits are washed to remove the excess WBC 1 and RBC 1, such as excess WBC 1 and RBC 1 that may be in the fluidics circuitry outside of the first incubation station 1314 and holding station 1316 respectively. The portions of the fluidics circuits may be washed with any suitable fluid, such as, in some instances, diluent and/or a cleaning fluid. In the particular embodiment shown, diluent (shown as a bolded line) is pumped from pumps 1310, 1336, 1338 such that diluent flows through mixing chambers 1306, 1308, and through valves 1318, 1320, 1322, 1324, 1326, 1330, 1332, 1334, some of which are configured such that diluent flow bypasses first incubation station 1314, second incubation station 1328, and holding station 1316. The diluent is then removed as waste. In some embodiments, the diluent is vacuumed out of the system (shown as a crisscross line) facilitated by vacuum pump 1340. In some embodiments, washing of excess WBC 1 and RBC 1 may take five second or less, or, in some embodiments approximately three seconds.

While not shown in a figure, after washing of excess WBC 1 and RBC 1 (or during overlapping time periods) diluent and/or cleaner may be washed through the flow cell. In one embodiment, diluent may be pumped from pump 1338, through valves 1332, 1334 (configured during this time segment to bypass holding station 1316), through additional lines and appropriately configured valves, and then ultimately through a common fluid pathway 1342 where it enters flow cell 1302. In some instances, a sheath fluid may also be flown through the flow cell 1302 at the same time, such as by one or both of the sheath fluid pumps 1344, 1346 shown in the figures. In some embodiments, washing of the flow cell may take five second or less, or, in some embodiments approximately two seconds.

Figure 13D:
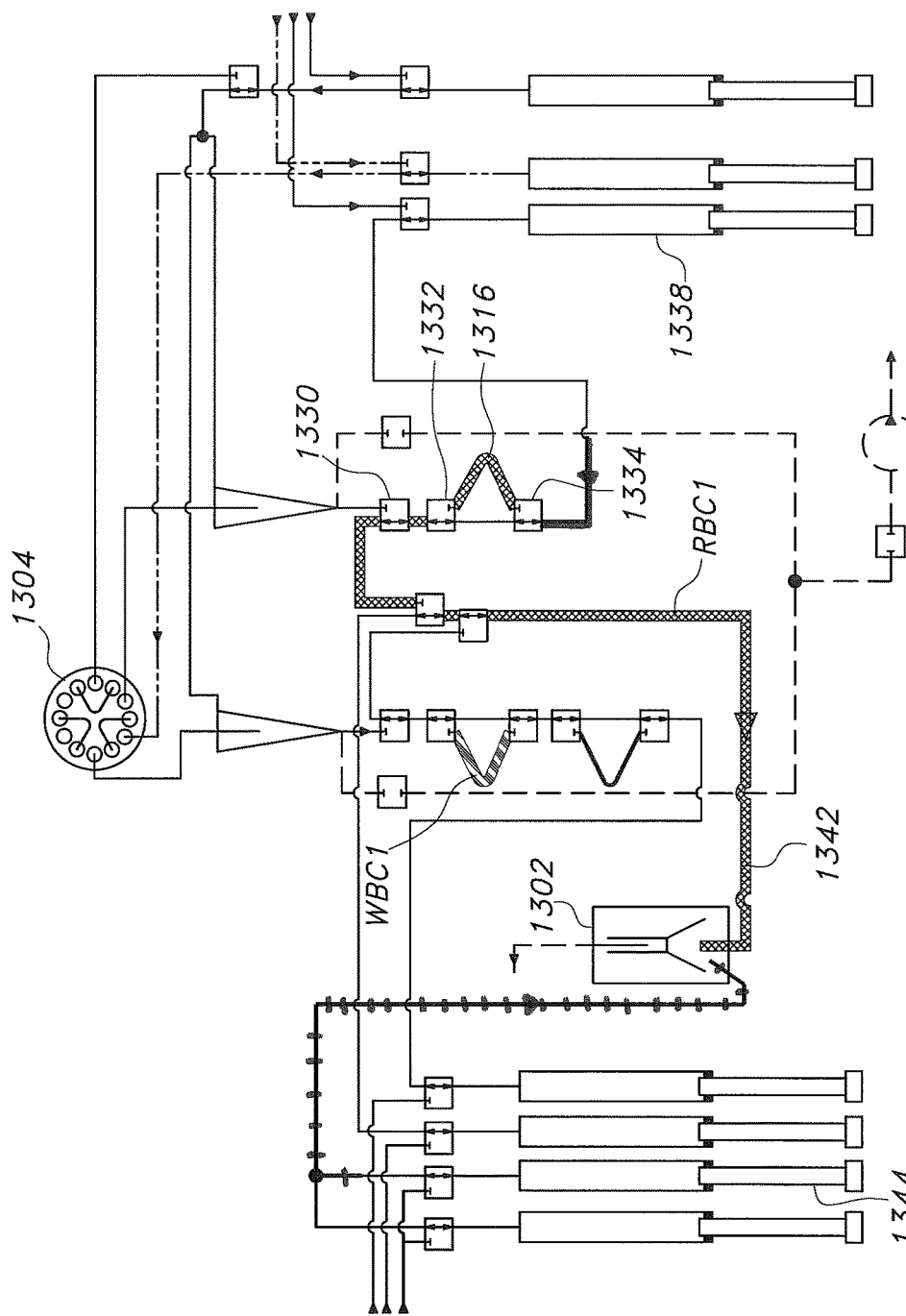

Turning to FIG. 13(d), the system may next begin to flow RBC 1 through the flow cell 1302. In the specific embodiment shown, valves including valves 1330, 1332, 1334, are configured such that pump 1338 may pump diluent into the holding station 1316 to begin to push RBC 1 out of the holding station 1316 and eventually into common fluid pathway 1342, where it enters flow cell 1302. At the same time, one of the sheath fluid pumps (e.g. 1344) may begin to (or continue to) pump sheath fluid (shown as a railroad line) through the flow cell 1302. In some embodiments, the initial push of RBC 1 through the flow cell 1302 occurs for approximately two seconds, and may be done prior to imaging in order to prime the pathway leading up to the flow cell and the cannula and other parts of the flow cell 1302.

Figure 13E:
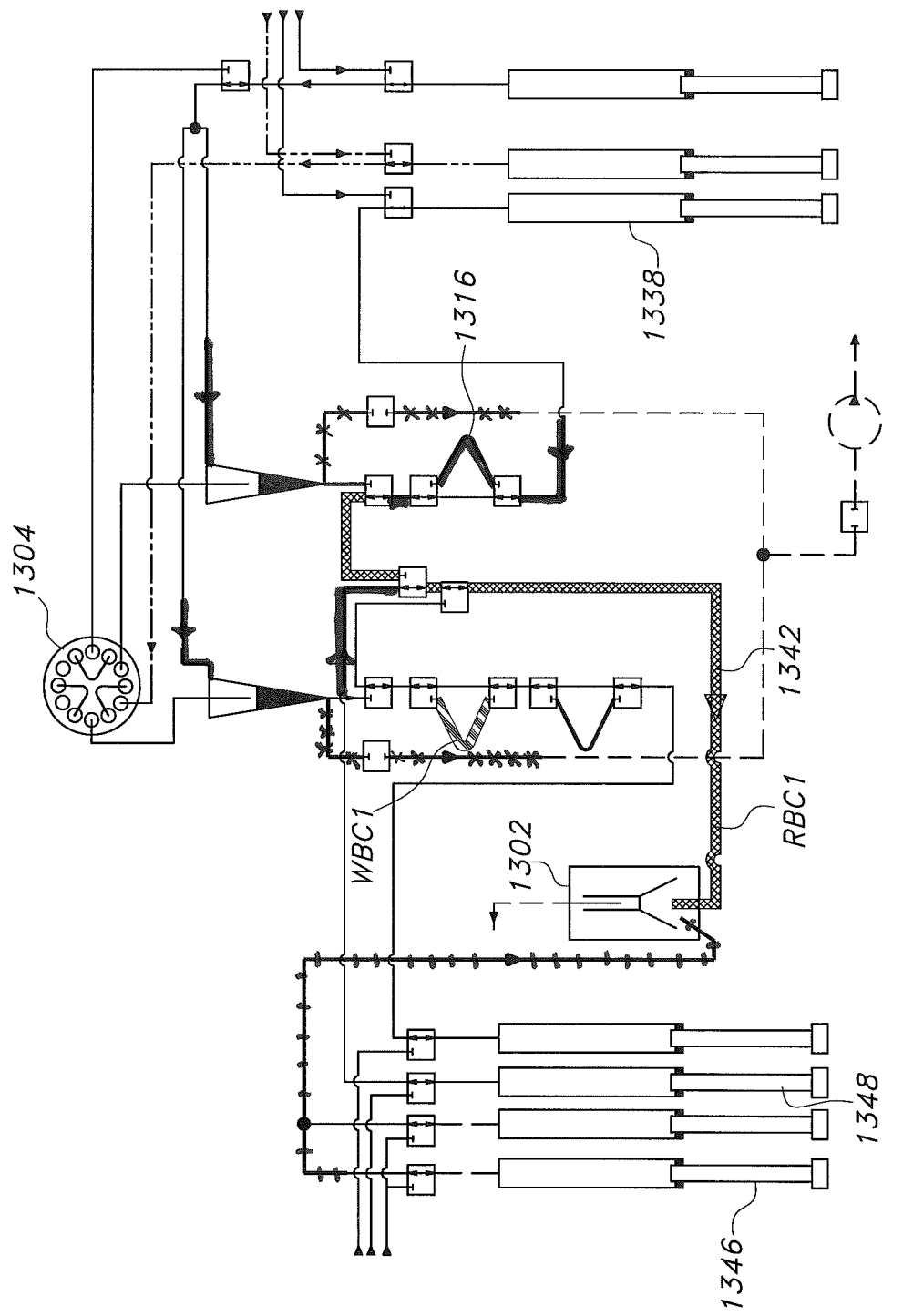

At FIG. 13(e), the system is imaging RBC 1 as it flows through flow cell 1302. In the specific embodiment shown, pump 1338 continues to pump diluent through holding station 1316 (with the valves configured appropriately) to continue to push RBC 1 through flow cell 1302, while one of the sheath fluid pumps (e.g. 1346) pumps sheath fluid through the flow cell 1302. In the specific embodiment shown, pump 1348 also pumps diluent through certain (appropriately configured) valves and common fluid pathway 1342 to facilitate pushing RBC 1 through flow cell 1302. In some embodiments, imaging will be completed prior to diluent from pump 1348 reaching the flow cell 1302. In some embodiments, the system images RBC 1 as it flows through flow cell 1302 for approximately 5 seconds. In other embodiments, the system images RBC sample portions for other time periods, such as a time period in the range of 1 to 30 seconds. In some embodiments, use of two sheath fluid pumps may facilitate providing a constant supply of sheath fluid to the flow cell 1302. In other embodiments, it is not necessary to have multiple sheath fluid pumps.

Figure 13F:
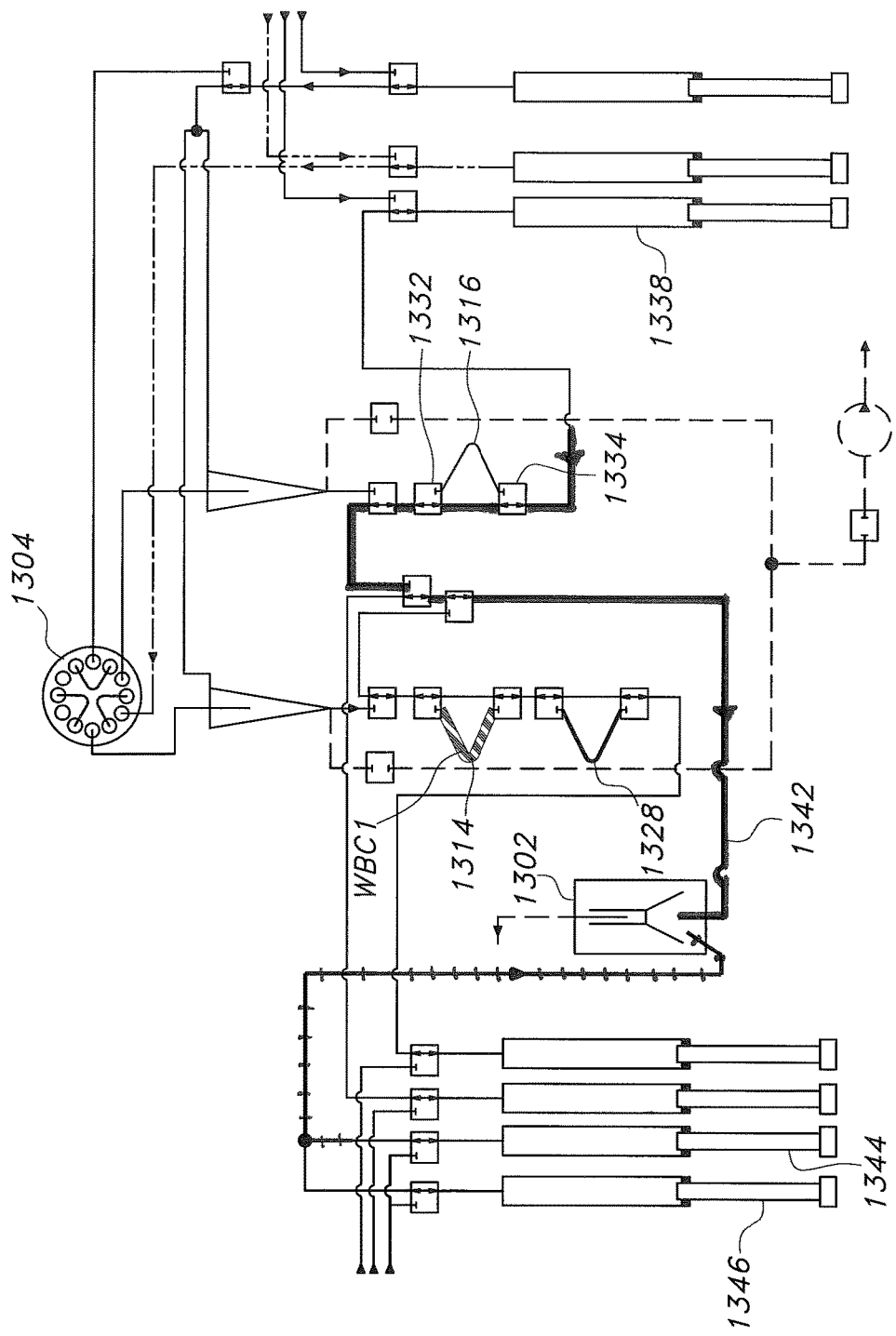

At FIG. 13(f), after RBC 1 has been imaged, diluent and/or cleaner is washed through the flow cell. In the specific embodiment shown, diluent is pumped from pump 1338, through valves 1332, 1334 (configured during this time segment to bypass holding station 1316), through additional lines and appropriately configured valves, and then ultimately through the common fluid pathway 1342 where it enters flow cell 1302. In the specific embodiment shown, the sheath fluid is also flowed through the flow cell 1302 at the same time, such as by one or both of the sheath fluid pumps 1344, 1346 shown in the figures. In some embodiments, washing of the flow cell may take five seconds or less, or, in some embodiments approximately two seconds.

While not shown in the figures, diluent and/or cleaner may subsequently be washed through the flow cell using pump 1336 to pump diluent and/or cleaner through the valves and other components proximate the first and second incubation stations 1314, 1328.

Figure 13G:
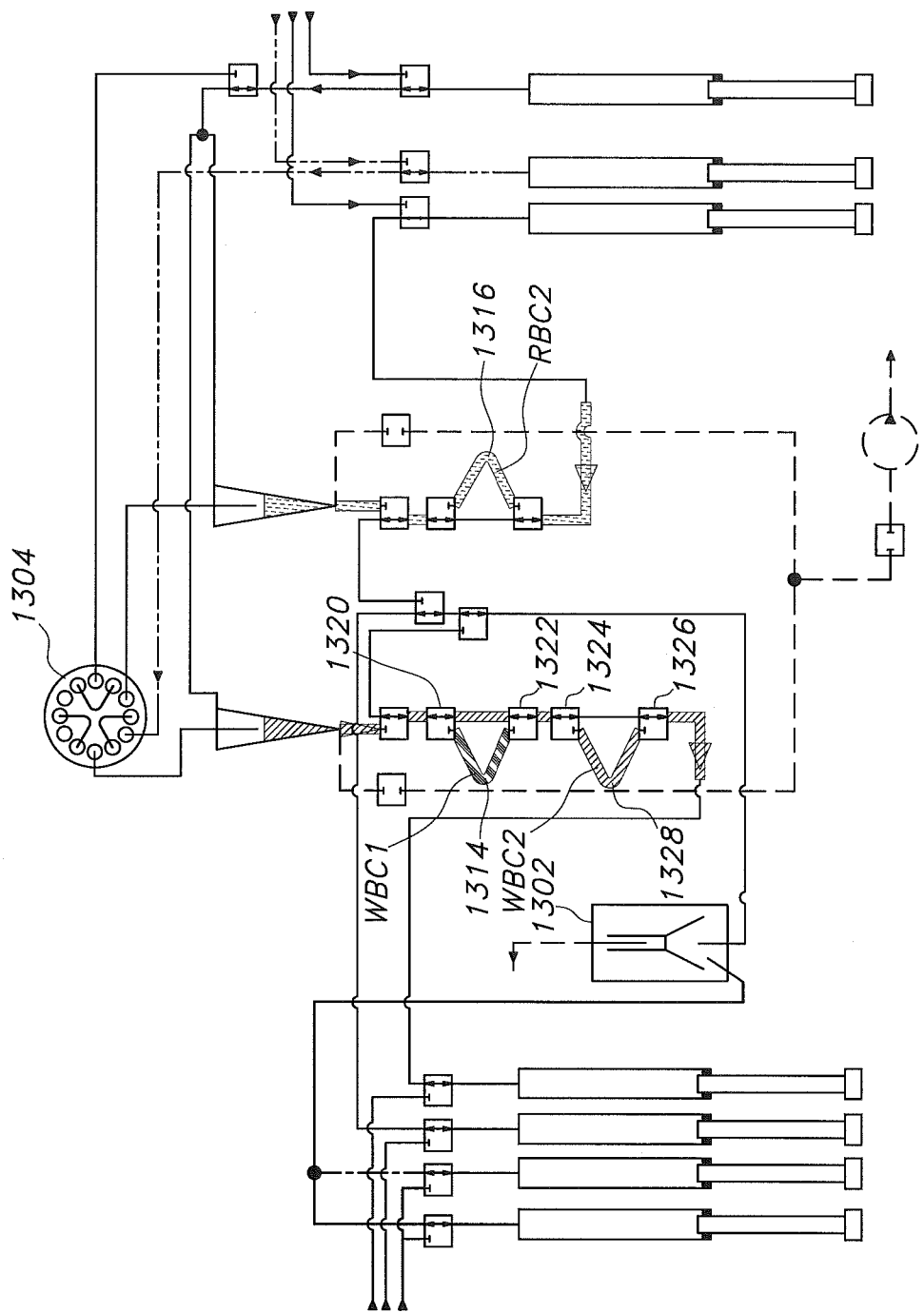

At FIG. 13(g), fluid sample portions WBC 2 (shown as a forward diagonal crosshatch line) and RBC 2 (shown as a dash crosshatch line) are loaded into second incubation station 1328 and holding station 1316 respectively (after having been mixed with reagent and/or diluent in a step not shown in the figures). WBC 2 and RBC 2 are loaded in similar manners to how WBC 1 and RBC 1 were loaded in a previously described step, except, for instance, that here, valves 1320, 1322, 1324, 1326 are configured such that WBC 2 bypasses first incubation station 1314 and enters second incubation station 1328. In some embodiments, sample portions are loaded into the system approximately every 30 seconds.

Figure 13H:
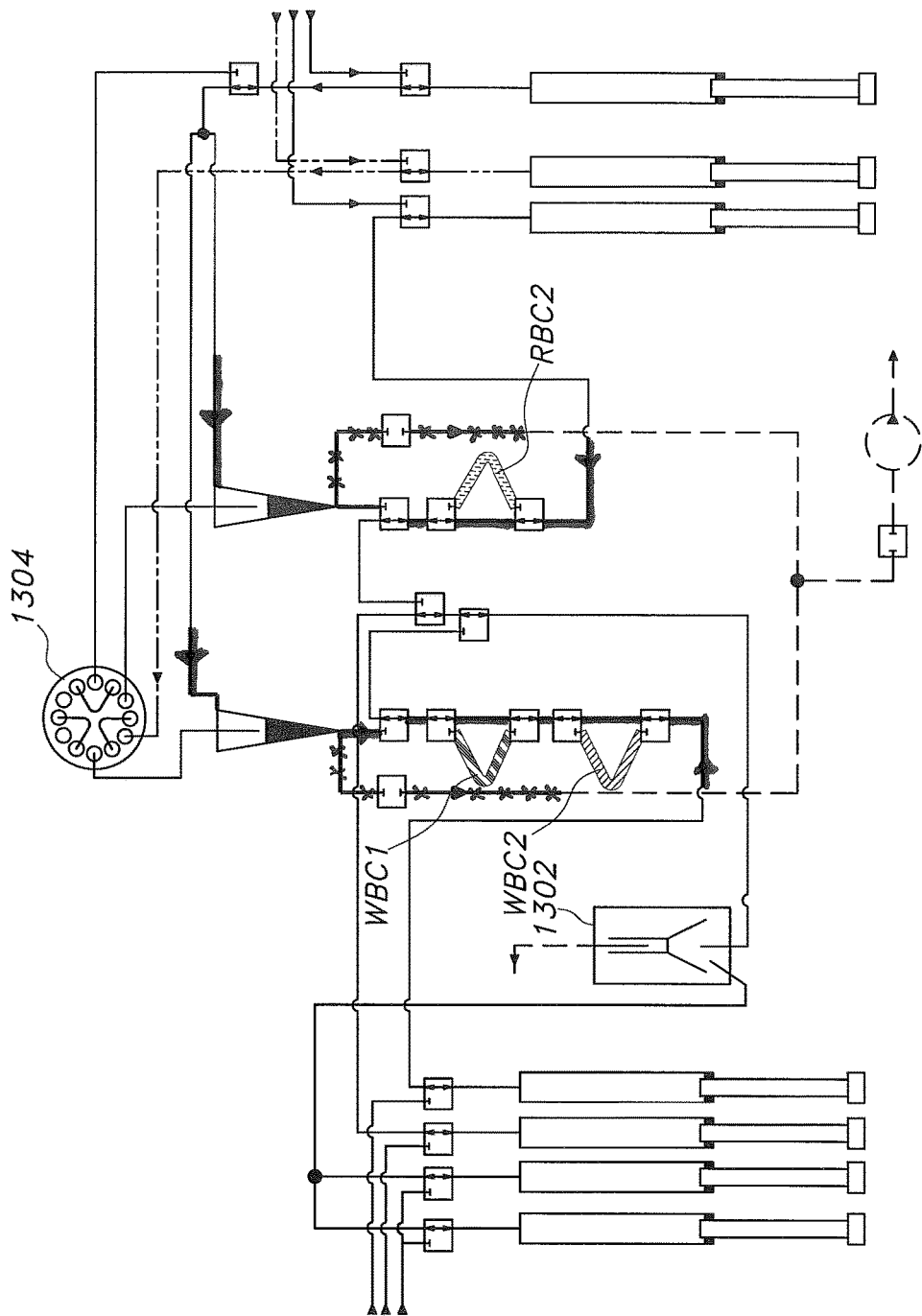

At FIG. 13(h), excess amounts of WBC 2 and RBC 2 are washed to waste in a similar manner to the washing step described above in FIG. 13(c).

Figure 13I:
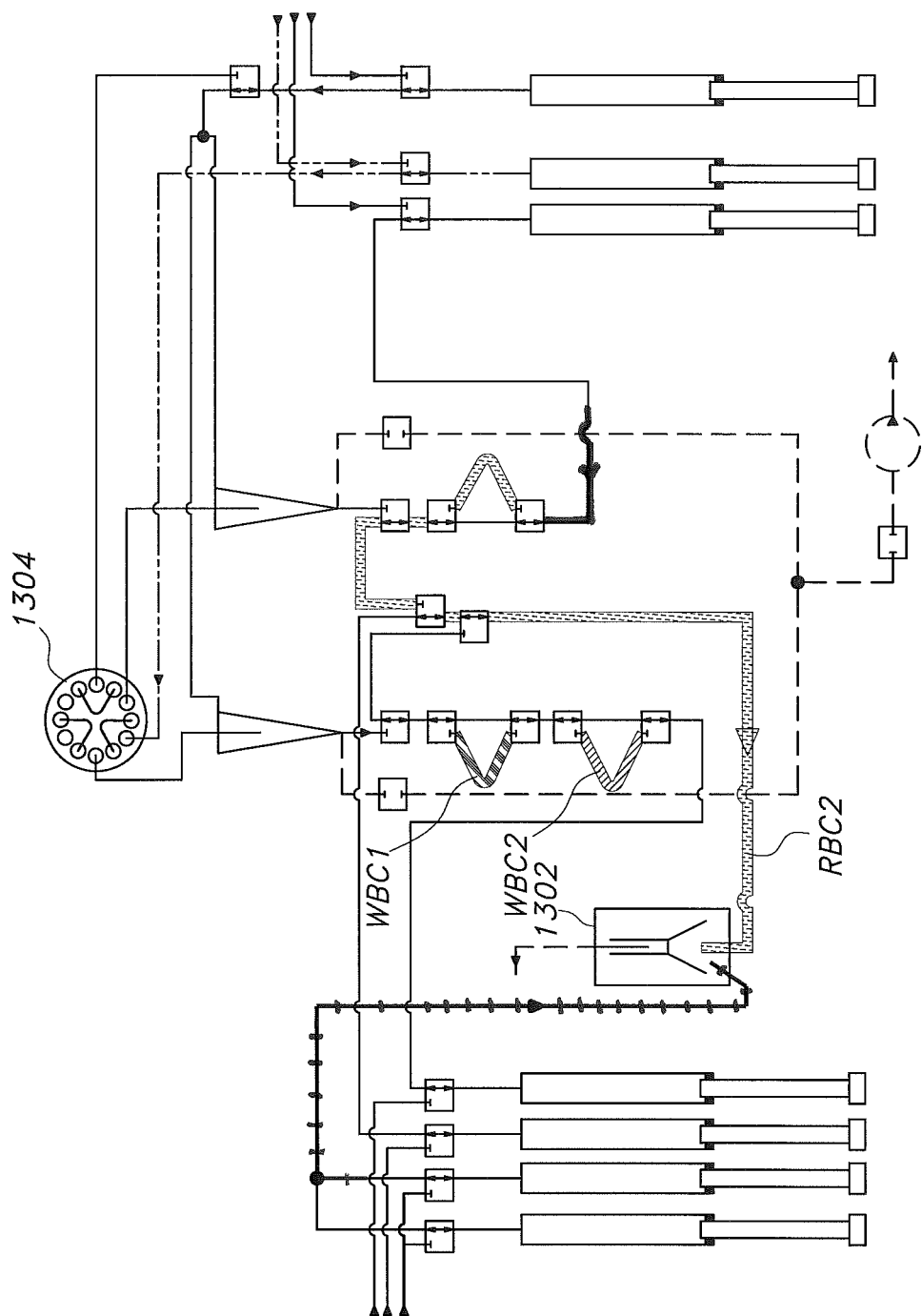

At FIG. 13(i), the system next begins to flow RBC 2 through the flow cell 1302 in a similar manner to that described above for FIG. 13(d).

Figure 13J:
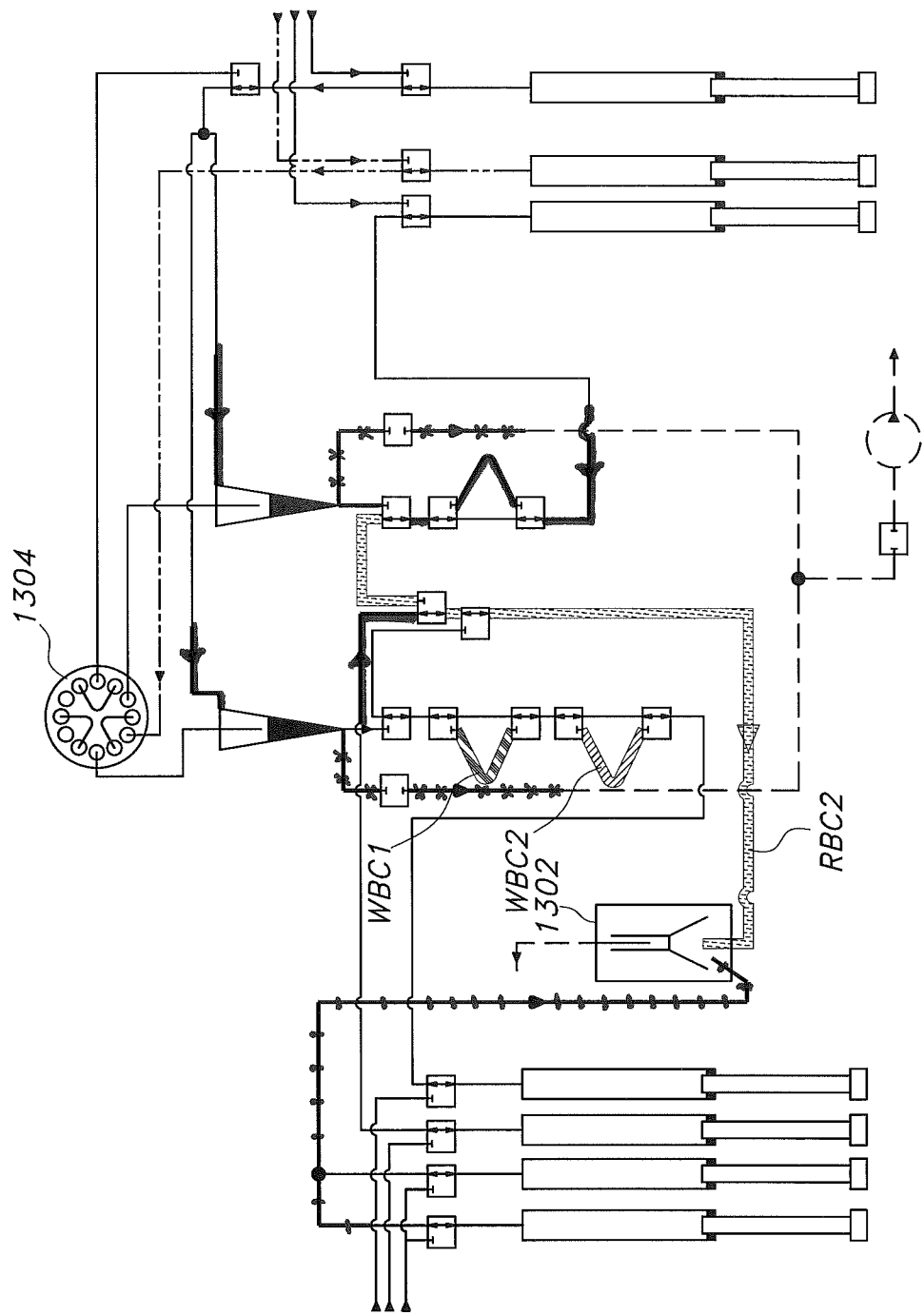

At FIG. 13(j), the system is imaging RBC 2 as it flows through flow cell 1302 in a similar manner to that described above for FIG. 13(e). It should be noted that, at this time in the process, two RBC fluid sample portions have now been imaged before WBC 1 has been imaged (including RBC 2, which was received in the system after WBC 1 was received and began being processed).

Figure 13K:
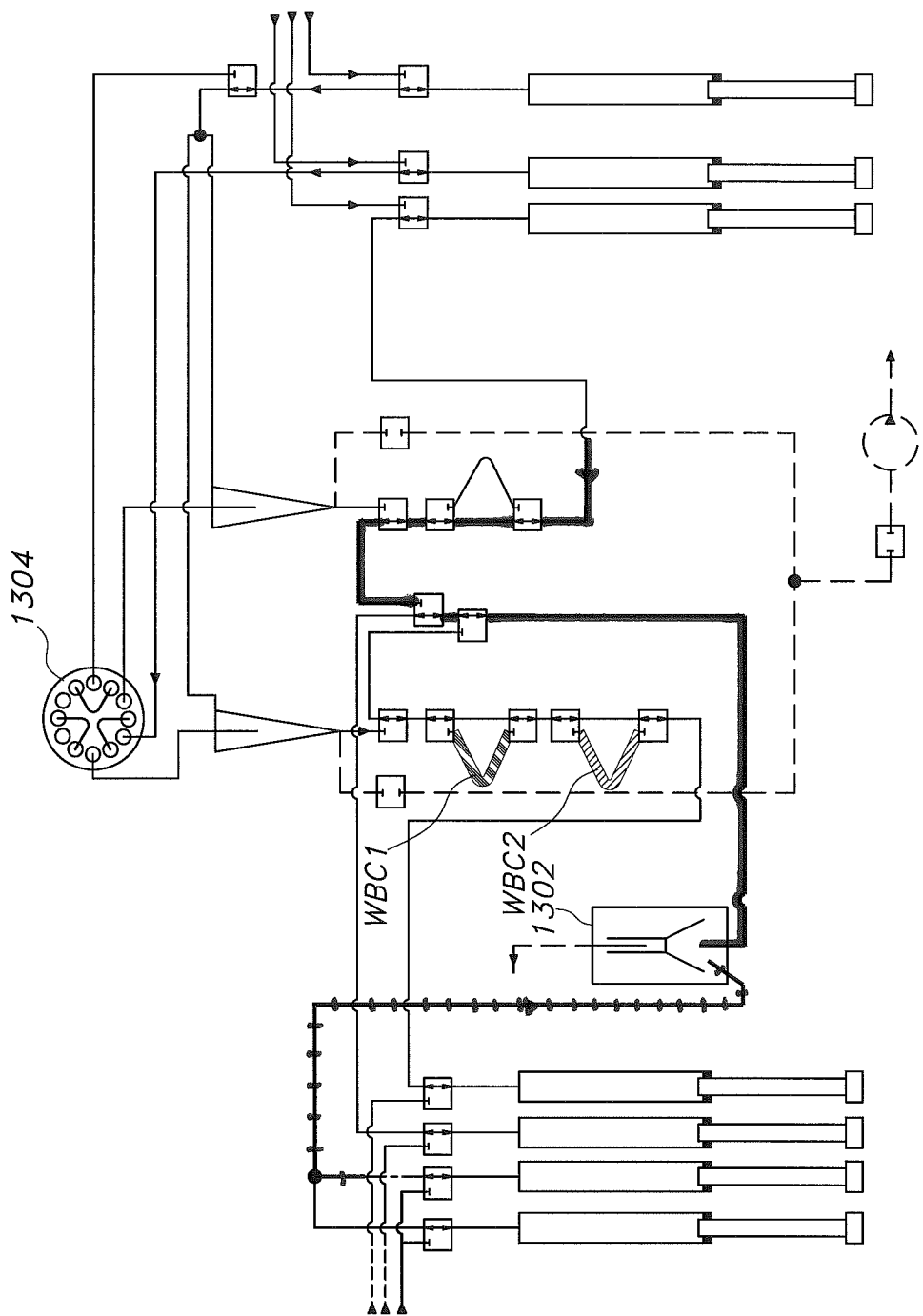

At FIG. 13(k), after RBC 2 has been imaged, diluent and/or cleaner is washed through the flow cell in a similar manner to that described for FIG. 13(f).

Figure 13L:
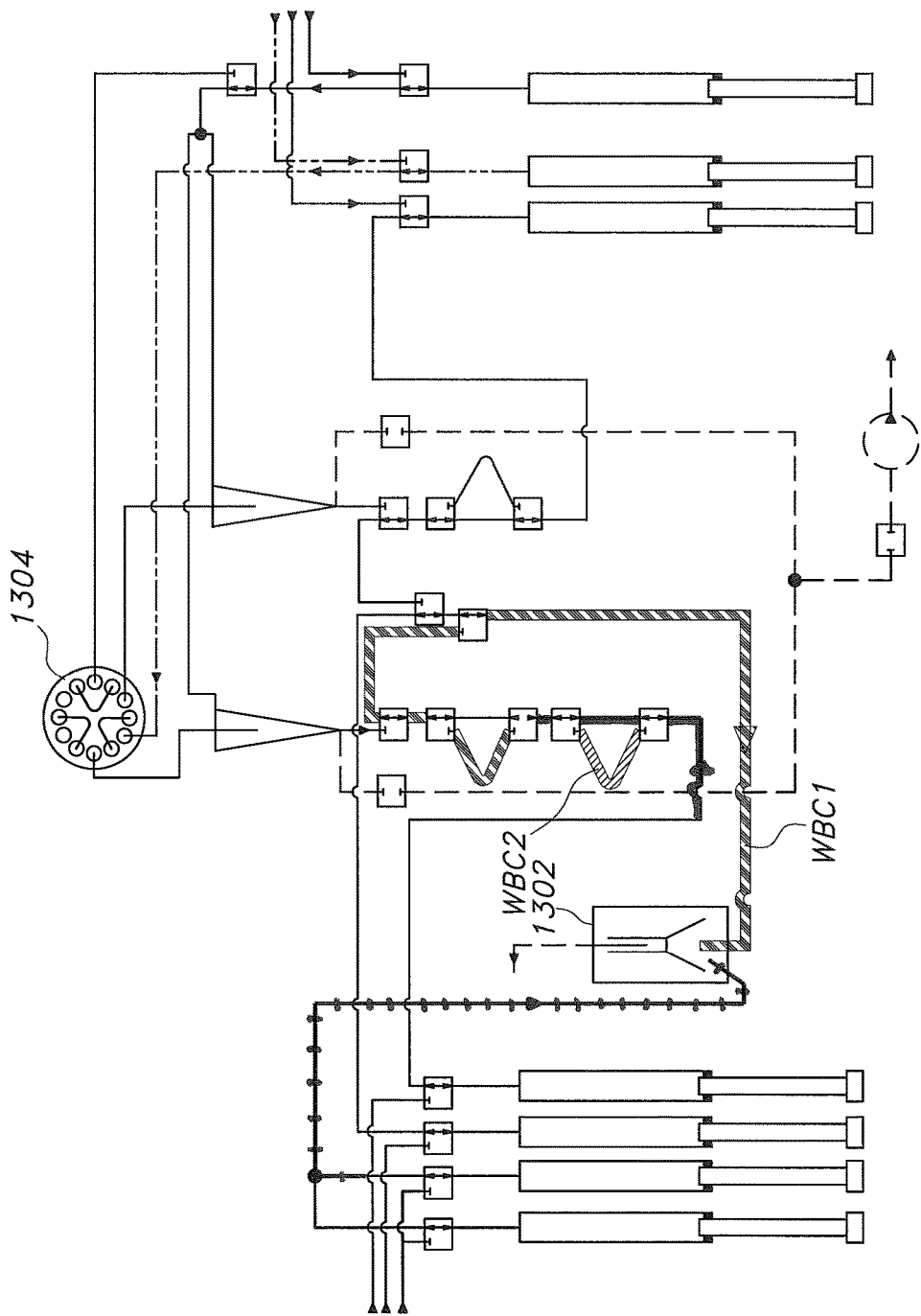

At FIG. 13(l), the system next begins to flow WBC 1 through the flow cell 1302 in a similar manner to that described above for FIG. 13(d). At this time in the process, WBC 1 has been in the system for approximately 50 seconds and incubating in the first incubation station for approximately 45 seconds.

Figure 13M:
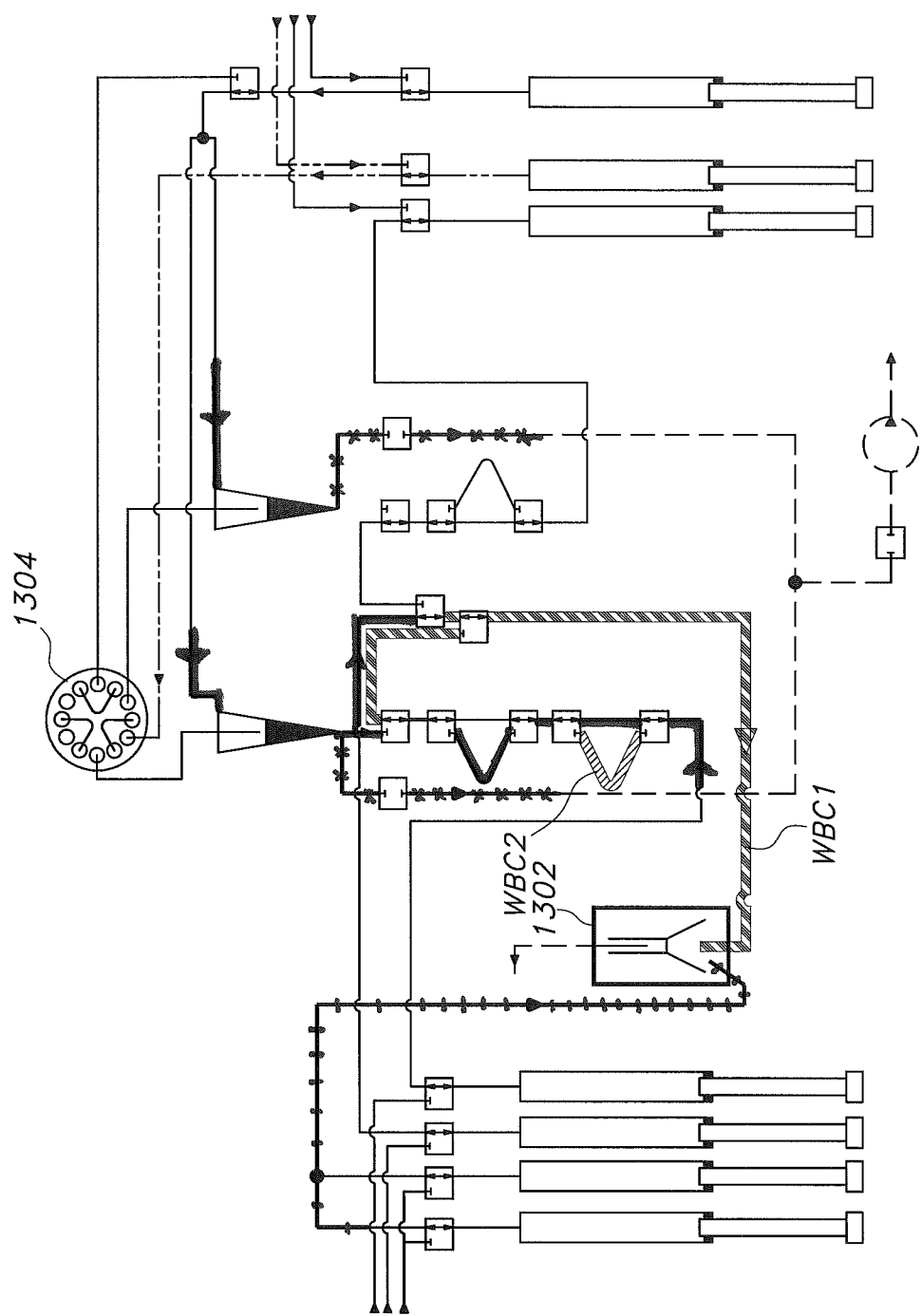

At FIG. 13(m), the system is imaging WBC 1 as it flows through flow cell 1302 in a similar manner to that described for FIG. 13(e).

While not shown in the figures, those of skill in the art will recognize that the steps illustrated in FIGS. 13(a)-13(m) may be repeated for additional samples. In some embodiments, sample portions may be imaged in the following order: RBC 1, RBC 2, WBC 1, RBC 3, WBC 2, RBC 4, WBC 3, RBC 5, WBC 4 . . . . In other words, two RBC sample portions may be initially imaged, followed by a WBC sample portion, with subsequent imagings alternating between RBC and WBC sample portions. In some embodiments, sample portions may be imaged in the following order: RBC 1, RBC 2, WBC 1, RBC 3, WBC 2, RBC 4, WBC 3, RBC 5, WBC 4 . . . . RBC N, WBC N−1, WBC N. In other words, two RBC sample portions may be initially imaged, followed by a WBC sample portion, with subsequent imagings alternating between RBC and WBC sample portions, with two WBC sample portions being imaged at the conclusion of the imaging of all the samples.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

The invention claimed is:

1. A system for imaging a plurality of blood fluid portions, the system comprising:
   a sample fluidic system having:
   a sample separator valve system,
   a first blood fluid pathway,
   a second blood fluid pathway separate from the first blood fluid sample pathway, and
   a common blood fluid pathway in fluid communication with the first and second blood fluid pathways, wherein the sample separator valve system is in fluid communication with the first and second blood fluid pathways and is configured to deliver a first blood fluid portion containing a first type of cell to the first blood fluid pathway and a second blood fluid portion to the second blood fluid pathway,
   wherein the first blood fluid pathway comprises a first processing station configured to process the first blood fluid portion so as to enhance the system's ability to image the first type of cell, wherein the first processing station processes the first blood fluid portion via mixing, staining, incubation, heating or any combination thereof; and
   a flow cell having a sample port operatively coupled with the common blood fluid pathway such that, when the first and second blood fluid portions are in the sample fluidic system, the first sample portion and the second sample portion are injected into the common pathway to the sample port along the first and second blood fluid pathways, respectively.

2. The system of claim 1, further comprising a dilution chamber in fluid communication with the valve system and the second blood fluid pathway, such that the valve system delivers the second blood fluid portion to the dilution chamber first before it is being delivered to the second blood fluid pathway.

3. The system of claim 2, further comprising:
   a diluent pump configured to inject a diluent to a substantial part of the second blood fluid pathway and to the dilution chamber, and
   a vacuum pump configured to evacuate the diluent in the dilution chamber and the substantial part of the second blood fluid pathway.

4. The system of claim 1, wherein the first processing station comprises a heating element to incubate the first blood fluid portion.

5. The system of claim 4, further comprising temperature sensors coupled to the flow cell or the fluidic system as to produce a temperature reading, and a controller configured to receive the temperature reading from the temperature sensors and to adjust operations of the heating element such that the first blood fluid portion in the first processing station is maintained at a desired temperature.

6. The system of claim 1, further comprising a diluent pump configured to inject a diluent to the second blood fluid pathway so as to deliver the second blood fluid portion to the common pathway.

7. The system of claim 6, further comprising a sample pump configured to inject a fluid to the common pathway so as to deliver the second blood fluid portion from the common pathway to the sample port of the flow cell.

8. The system of claim 1,
   wherein the second blood fluid portion comprises the first type of cell,
   the second blood fluid pathway comprises a second processing station configured to process the second blood fluid portion so as to enhance the system's ability to image the first type of cell, wherein the second processing station processes the second blood fluid portion via mixing, staining, incubation, heating or any combination thereof, and
   the first blood fluid portion is directed to the first processing pathway by opening first and second control valves located at the first processing station and closing third and fourth control valves located at the second processing station.

9. The system of claim 1,
   wherein the second blood fluid portion comprises the first type of cell,
   the second blood fluid pathway comprises a second processing station configured to process the second blood fluid portion so as to enhance the system's ability to image the first type of cell, wherein the second processing station processes the second blood fluid portion via mixing, staining, incubation, heating or any combination thereof, and
   the second blood fluid portion is directed to the second blood fluid pathway by closing the first and the second control valves located at the first processing station and opening the third and the fourth control valves located at the second processing station.

10. The system of claim 9, further comprising a bypass pathway bypassing the first blood fluid pathway, wherein the second blood fluid portion is directed to the second blood fluid pathway through the bypass pathway.

11. The system of claim 1, wherein the second blood fluid portion comprises red blood cells, and the valve system separates the fluidic system into the first blood fluid pathway and the second blood fluid pathway, the second blood fluid pathway including a holding station for holding a predetermined volume of the second blood fluid portion.

12. The system of claim 11, wherein the holding station comprises a tubing loop and a pair of holding station valves at ends of the tubing loop.

13. A method for imaging a plurality of blood fluid portions, the method comprising:
   receiving at least a portion of a first sample into an internal fluidic system of a sample analysis system;
   after receiving the portion of the first sample into the internal fluidic system, receiving at least a portion of a second sample into the internal fluidic system;
   after receiving the first and second samples into the internal fluidic system, flowing the portion of the second sample through a flow cell and imaging the portion of the second sample as it flows through the flow cell;
   after flowing the portion of the second sample through the flow cell, flowing the portion of the first sample through the flow cell,
   wherein the imaging further comprises flowing portions of the first or second samples or both through a processing station configured to process the portions of the samples so as to enhance the system's ability to image cells in the sample, wherein the processing station processes the portions of the samples via mixing staining, incubation, heating or any combination thereof.

14. A system for imaging a plurality of blood fluid portions, the system comprising:
   a sample fluidic system having:
   a sample separator valve system,
   a first blood fluid pathway, a second blood fluid pathway separate from the first blood fluid sample pathway, and a common blood fluid pathway in fluid communication with the first and second blood fluid pathways, wherein the sample separator valve system is in fluid communication with the first and second blood fluid pathways and is configured to deliver a first blood fluid portion containing a first type of cell to the first blood fluid pathway and a second blood fluid portion to the second blood fluid pathway, a dilution chamber in fluid communication with the valve system and the second blood fluid pathway, such that the valve system delivers the second blood fluid portion to the dilution chamber first before it is being delivered to the second blood fluid pathway, wherein the first blood fluid pathway comprises a first processing station configured to process the first blood fluid portion so as to enhance the system's ability to image the first type of cell; and a flow cell having a sample port operatively coupled with the common blood fluid pathway such that, when the first and second blood fluid portions are in the sample fluidic system, the first sample portion and the second sample portion are injected into the common pathway to the sample port along the first and second blood fluid pathways, respectively.

15. The system of claim 14, wherein the first processing station comprises a heating element to incubate the first blood fluid portion.

16. The system of claim 14, further comprising a diluent pump configured to inject a diluent to the second blood fluid pathway so as to deliver the second blood fluid portion to the common pathway.

17. The system of claim 14,
wherein the second blood fluid portion comprises the first type of cell,
the second blood fluid pathway comprises a second processing station configured to process the second blood fluid portion so as to enhance the system's ability to image the first type of cell, wherein the second processing station processes the second blood fluid portion via mixing, staining, incubation, heating or any combination thereof, and
the first blood fluid portion is directed to the first processing pathway by opening first and second control valves located at the first processing station and closing third and fourth control valves located at the second processing station.

18. The system of claim 14,
wherein the second blood fluid portion comprises the first type of cell,
the second blood fluid pathway comprises a second processing station configured to process the second blood fluid portion so as to enhance the system's ability to image the first type of cell, wherein the second processing station processes the second blood fluid portion via mixing, staining, incubation, heating or any combination thereof, and
the second blood fluid portion is directed to the second blood fluid pathway by closing the first and the second control valves located at the first processing station and opening the third and the fourth control valves located at the second processing station.

19. The system of claim 14, further comprising a bypass pathway bypassing the first blood fluid pathway, wherein the second blood fluid portion is directed to the second blood fluid pathway through the bypass pathway.

20. The system of claim 14, wherein the second blood fluid portion comprises red blood cells, and the valve system separates the fluidic system into the first blood fluid pathway and the second blood fluid pathway, the second blood fluid pathway including a holding station for holding a predetermined volume of the second blood fluid portion.

* * * * *